United States Patent
Mototsu et al.

(10) Patent No.: US 8,951,803 B2
(45) Date of Patent: Feb. 10, 2015

(54) SAMPLE ANALYZER AND SAMPLE ANALYZING METHOD

(75) Inventors: Kazunori Mototsu, Kobe (JP); Teruyuki Uekawa, Himeji (JP)

(73) Assignee: Sysmex Corporation, Hyogo (JP)

( * ) Notice: Subject to any disclaimer, the term of this patent is extended or adjusted under 35 U.S.C. 154(b) by 831 days.

(21) Appl. No.: 12/893,714

(22) Filed: Sep. 29, 2010

(65) Prior Publication Data
US 2011/0076774 A1 Mar. 31, 2011

(30) Foreign Application Priority Data
Sep. 30, 2009 (JP) .................. 2009-227599

(51) Int. Cl.
*G01N 35/00* (2006.01)
*G01N 33/00* (2006.01)
*G01N 35/04* (2006.01)

(52) U.S. Cl.
CPC ........ *G01N 35/04* (2013.01); *G01N 2035/0455* (2013.01); *G01N 2035/0443* (2013.01); *G01N 2446/00* (2013.01); *G01N 2035/00465* (2013.01); *G01N 2035/0458* (2013.01)
USPC ................. 436/43; 436/45; 436/174; 422/64; 422/68.1

(58) Field of Classification Search
None
See application file for complete search history.

(56) References Cited

U.S. PATENT DOCUMENTS

| 3,901,656 | A | * | 8/1975 | Durkos et al. ................. 436/47 |
| 5,451,528 | A | * | 9/1995 | Raymoure et al. ............ 436/533 |
| 2002/0132353 | A1 | | 9/2002 | Tamura et al. |
| 2008/0095668 | A1 | * | 4/2008 | Mototsu et al. ............. 422/68.1 |
| 2008/0241939 | A1 | * | 10/2008 | Matsuo et al. ................. 436/54 |

FOREIGN PATENT DOCUMENTS

| JP | 2008-096223 A | 4/2008 |
| WO | 93/20444 A1 | 10/1993 |

* cited by examiner

*Primary Examiner* — Yelena G Gakh
*Assistant Examiner* — Michelle Adams
(74) *Attorney, Agent, or Firm* — Sughrue Mion, PLLC

(57) ABSTRACT

A sample analyzer comprising: a reagent container holder, configured to rotate around a rotational axis and to hold a reagent container containing a reagent; a reagent aspirator for aspirating, at a reagent aspirating position, the reagent from the reagent container held by the reagent container holder; an analysis section for analyzing a measurement sample prepared from the reagent aspirated by the reagent aspirator and a sample; and a controller for controlling: the reagent container holder to rotate and thereby transport the reagent container to the reagent aspirating position, the reagent aspirator to aspirate the reagent from the reagent container, and the reagent container holder to accelerate and decelerate alternately while being rotated is disclosed. A sample analyzing method is also disclosed.

8 Claims, 14 Drawing Sheets

SAMPLE ANALYZER AND SAMPLE ANALYZING METHOD

RELATED APPLICATIONS

This application claims priority under 35 U.S.C. §119 to Japanese Patent Application No. 2009-227599 filed on Sep. 30, 2009, the entire content of which is hereby incorporated by reference.

FIELD OF THE INVENTION

The present invention relates to a sample analyzer and a sample analyzing method. The present invention particularly relates to a sample analyzer that includes a mechanism for agitating a reagent and a sample analyzing method.

BACKGROUND

Conventionally, there is a known sample analyzer that includes a mechanism for agitating a reagent (see, e.g., US patent application publication 2002-0132353).

The sample analyzer disclosed in US patent application publication 2002-0132353 includes an agitation mechanism. In the agitation mechanism, reagent containers are mounted and arranged in an annular manner on a turntable. The turntable is caused to rotate such that the reagent containers thereon rotate around the rotational center of the turntable. Also, each reagent container is caused to rotate on its axis on the turntable. In this manner, microparticles contained in the reagent of each reagent container are uniformly dispersed.

SUMMARY OF THE INVENTION

The first aspect of the presented invention is a sample analyzer comprising: a reagent container holder, configured to rotate around a rotational axis and to hold a reagent container containing a reagent; a reagent aspirator for aspirating, at a reagent aspirating position, the reagent from the reagent container held by the reagent container holder; an analysis section for analyzing a measurement sample prepared from the reagent aspirated by the reagent aspirator and a sample; and a controller for controlling: the reagent container holder to rotate and thereby transport the reagent container to the reagent aspirating position, the reagent aspirator to aspirate the reagent from the reagent container, and the reagent container holder to accelerate and decelerate alternately while being rotated.

The second aspect of the presented invention is a sample analyzer comprising: a reagent container holder, configured to rotate around a rotational axis and to hold a reagent container containing a reagent; a reagent aspirator for aspirating the reagent from the reagent container held by the reagent container holder; an analysis section for analyzing a measurement sample prepared from the reagent aspirated by the reagent aspirator and a sample; and a controller for controlling the reagent container holder, wherein the controller performs operations comprising: a first aspirating operation of controlling the reagent container holder to rotate the reagent container toward a reagent aspirating position at which the reagent aspirator aspirates the reagent; a second aspirating operation of controlling the reagent container holder to rotate the reagent container toward the reagent aspirating position; and an agitating operation of controlling, during an interval between the first aspirating operation and the second aspirating operation, the reagent container holder to accelerate and decelerate alternately while being rotated.

The third aspect of the present invention is a sample analyzer comprising: a reagent container holder, configured to rotate around a rotational axis and to hold a reagent container containing a reagent; a reagent aspirator for aspirating the reagent from the reagent container held by the reagent container holder; an analysis section for analyzing a measurement sample prepared from the reagent aspirated by the reagent aspirator and a sample; a driver for driving the reagent container holder; and a controller for controlling the driver, wherein the controller controls operations comprising: a first aspirating operation of controlling the reagent container holder to rotate the reagent container toward a reagent aspirating position at which the reagent aspirator aspirates the reagent; a second aspirating operation of controlling the reagent container holder to rotate the reagent container toward the reagent aspirating position; and an agitating operation of controlling, during an interval between the first aspirating operation and the second aspirating operation, the reagent container holder to rotate and thereby apply an inertia force intermittently to the reagent container.

The fourth aspect of the present invention is a sample analyzing method comprising: setting a reagent container containing a reagent to a reagent container holder, which is configured to rotate around a rotational axis while holding the reagent container; in a first rotation operation, causing the reagent container holder alternately to accelerate and to decelerate while rotating; in a second rotation operation, causing the reagent container holder to rotate the reagent container to a predetermined reagent aspirating position; and analyzing a measurement sample that is prepared from the reagent aspirated from the reagent container located at the predetermined reagent aspirating position and a sample.

The fifth aspect of the present invention is a sample analyzer comprising: a reagent container holder configured to rotate around a rotational axis while holding at least one reagent container; a driver arranged to alternately accelerate and decelerate the reagent container holder each more than once while the reagent container holder rotates around the rotational axis to a predetermined reagent aspirating position; and a section configured to aspirate a reagent from the reagent container and to analyze a sample comprising the aspirated reagent.

DESCRIPTION OF THE PREFERRED EMBODIMENTS

Hereinafter, a sample analyzer according to an embodiment of the present invention will be described in detail with reference to the accompanying drawings.

First, a configuration of an analyzer 1 according to the embodiment of the present invention is described with reference to FIGS. 1 to 12, 15, and 18.

The analyzer 1 according to the embodiment of the present invention performs tests on a sample (e.g., a blood sample) for various items such as hepatitis B, hepatitis C, tumor markers, thyroid hormones, and the like. In the analyzer 1, a capture antibody (R1 reagent) bound to an antigen contained in a sample (e.g., a blood sample) to be measured is bound to magnetic particles (R2 reagent), and the antigen, the capture antibody, and the magnetic particles, which have been bound, are attracted to a magnet (not shown) of a primary BF (Bound Free) separator 11 (see FIG. 1 and FIG. 2). In this manner, the R1 reagent containing the capture antibody that is unreacted (i.e., free) is removed. Then, the antigen bound to the magnetic particles is bound to a labeled antibody (R3 reagent). Thereafter, the magnetic particles, the antigen, and the labeled antibody, which have been bound, are attracted to a magnet (not shown) of a secondary BF separator 12. In this manner, the R3 reagent containing the labeled antibody that is unreacted (i.e., free) is removed. Further, a dispersion liquid (R4 reagent) and a luminescent substrate (R5 reagent) which emits light in a reaction process with the labeled antibody are added. Thereafter, the amount of light generated by the reaction of the luminescent substrate with the labeled antibody is measured. Through this process, the antigen contained in the sample, which is bound to the labeled antibody, is quantitatively measured.

Figure 1:
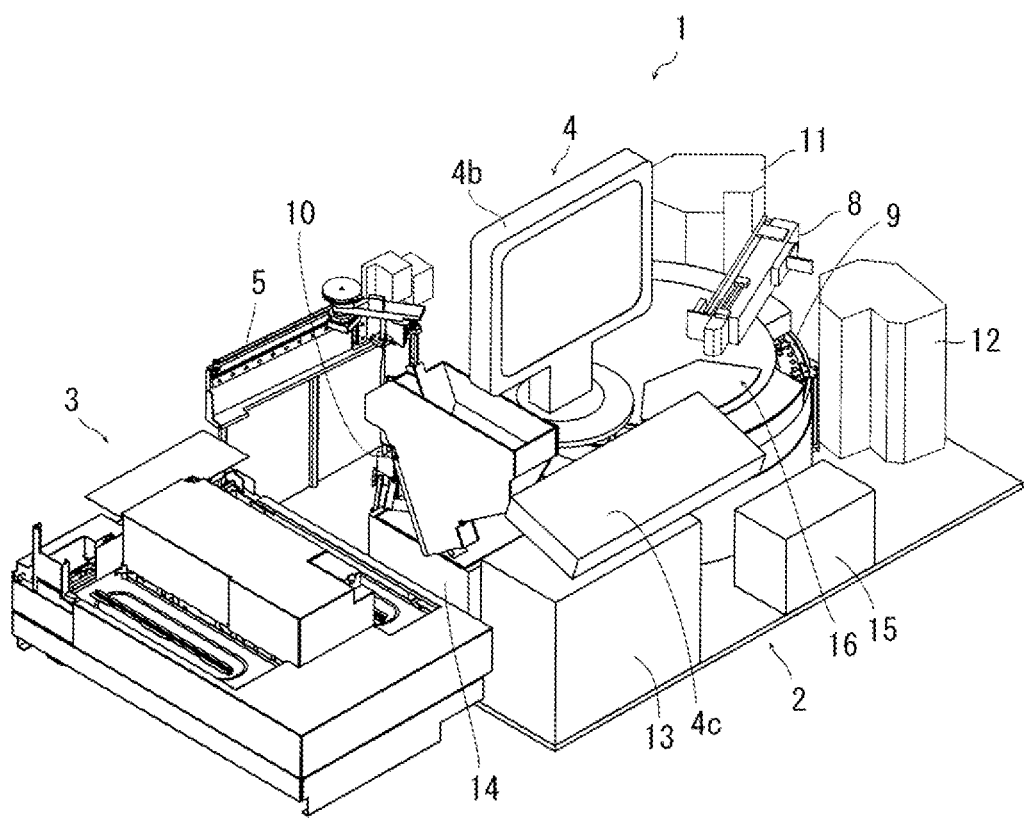
FIG. 1 is a perspective view showing the entire structure of an analyzer according to an embodiment of the present invention.
Figure 2:
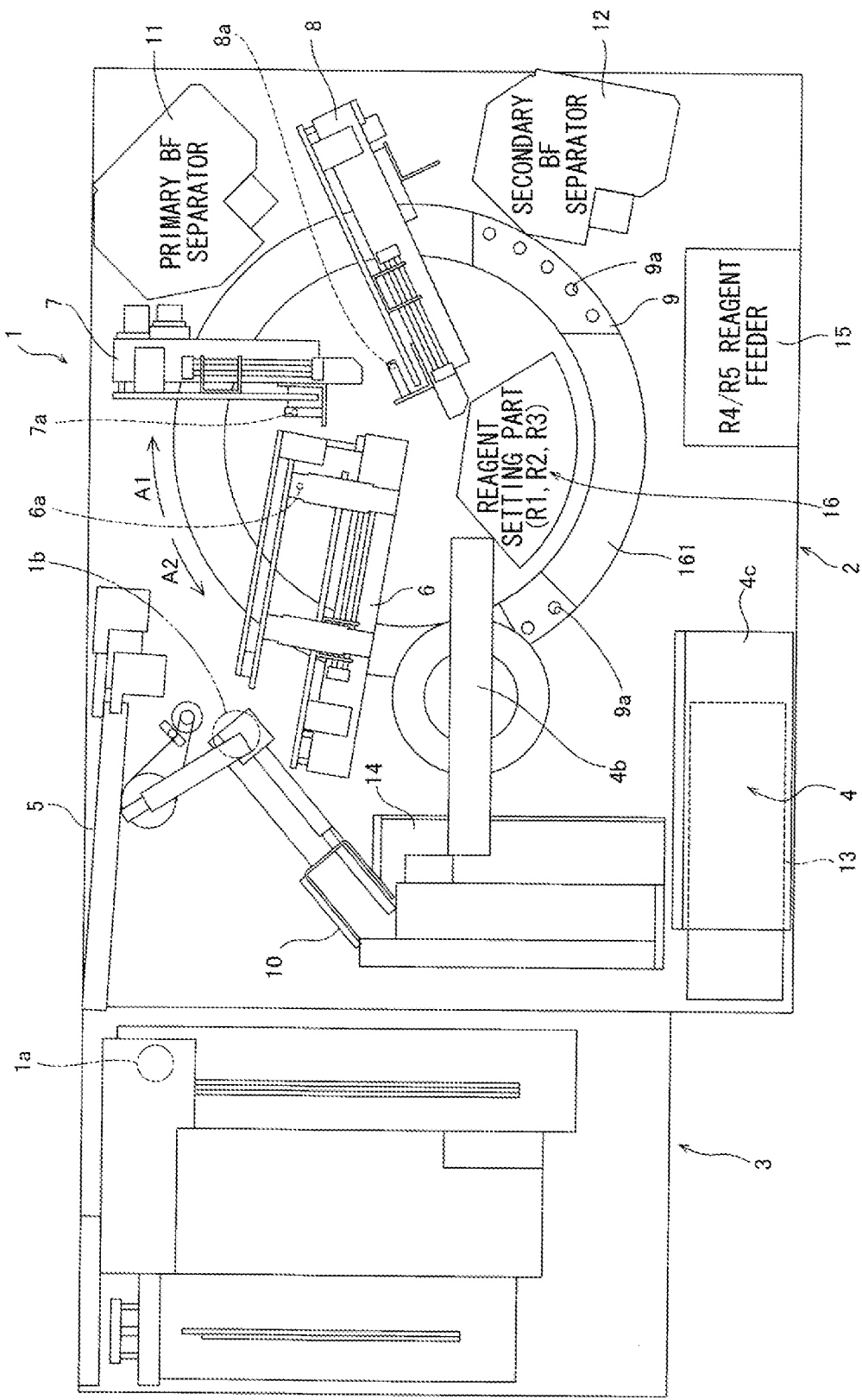
FIG. 2 is a plan view showing the entire structure of the analyzer according to the embodiment shown in FIG. 1.

As shown in FIG. 1 and FIG. 2, the analyzer 1 includes: a measurement mechanism unit 2; a sample transporting unit (sampler) 3 disposed adjacent to the measurement mechanism unit 2; and a control apparatus 4 which includes a PC (personal computer) electrically connected to the measurement mechanism unit 2.

Figure 3:
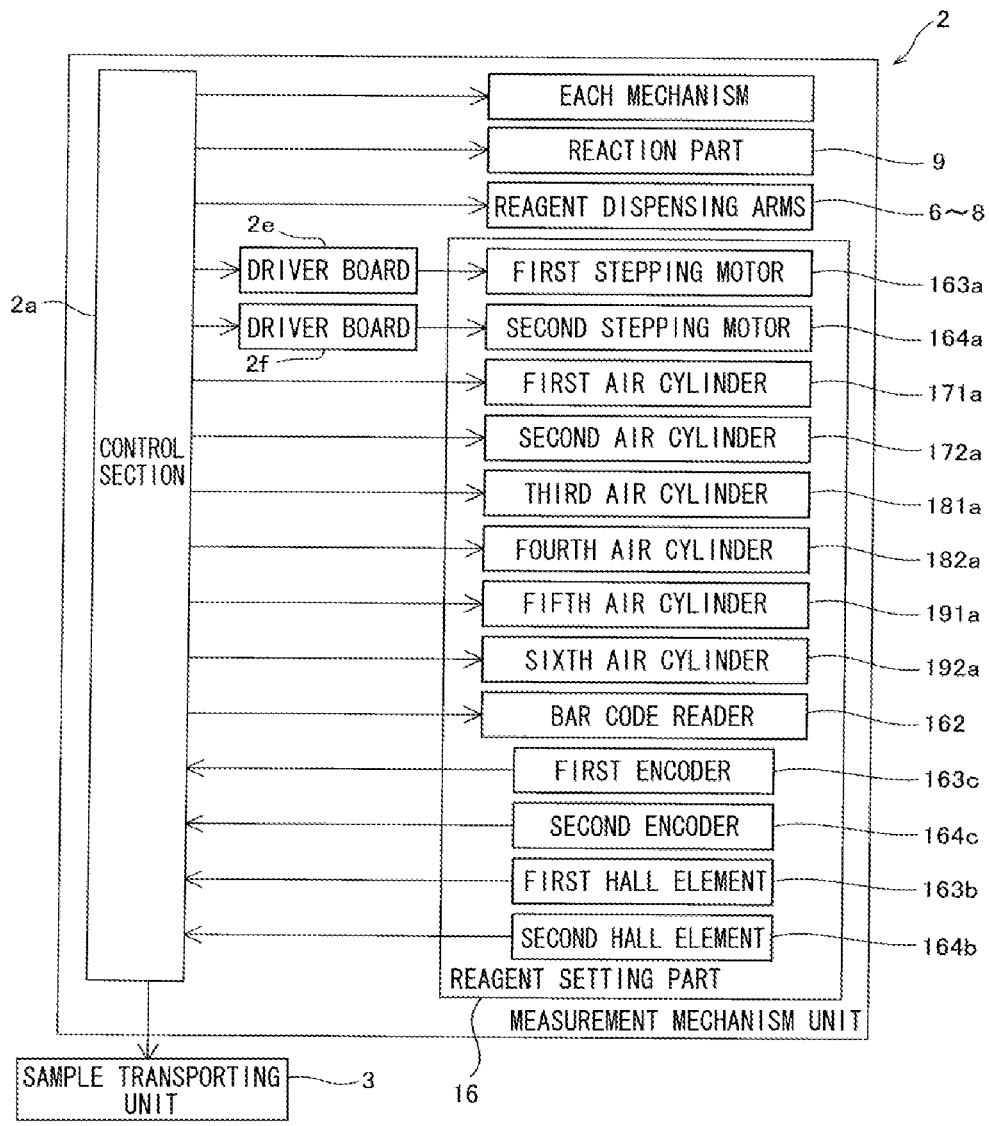
FIG. 3 is a block diagram showing a measurement mechanism unit of the analyzer according to the embodiment shown in FIG. 1.

The measurement mechanism unit 2 includes a sample dispensing arm 5, an R1 reagent dispensing arm 6, an R2 reagent dispensing arm 7, an R3 reagent dispensing arm 8, a reaction part 9, a cuvette feeder 10, the primary BF separator 11, the secondary BF separator 12, a pipette tip feeder 13, a detector 14, an R4/R5 reagent feeder 15, and a reagent setting part 16. As shown in FIG. 3, each mechanism in the measurement mechanism unit 2 (i.e., each dispensing arm, the reaction part 9, the reagent setting part 16, or the like) is controlled by a control section 2a of the measurement mechanism unit 2. The sample transporting unit 3 is also configured to be controlled by the control section 2a.

Figure 4:
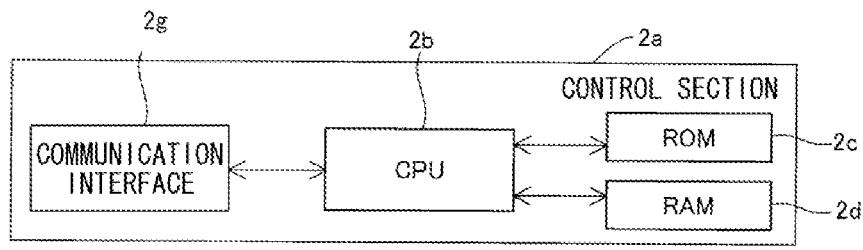
FIG. 4 is a block diagram showing a control section of the measurement mechanism unit of the analyzer according to the embodiment shown in FIG. 1.

As shown in FIG. 4, the control section 2a mainly includes a CPU 2b, a ROM 2c, a RAM 2d, and a communication interface 2g. The CPU 2b is configured to execute a computer program stored in the ROM 2c and a computer program loaded to the RAM 2d. The ROM 2c stores computer programs to be executed by the CPU 2b, data used for the execution of the computer programs, and the like. The RAM 2d is used for loading the computer programs stored in the ROM 2c. The RAM 2d is used as a work area for the CPU 2b at the time of execution of these computer programs. The communication interface 2g is connected to the control apparatus 4, and has functions to transmit optical information about a sample (i.e., data of the amount of light generated by the reaction between the labeled antibody and the luminescent substrate) to the control apparatus 4 and to receive signals from a control section 4a of the control apparatus 4. The communication interface 2g also has a function to transmit instructions which the CPU 2b provides in order to drive the sample transporting unit 3 and the measurement mechanism unit 2.

The sample transporting unit 3 is configured to transport a rack which accommodates multiple test tubes containing samples. Further, the sample transporting unit 3 is configured to transport a test tube containing a sample to a sample aspirating position 1a (see FIG. 2) at which the sample dispensing arm 5 aspirates the sample.

Figure 5:
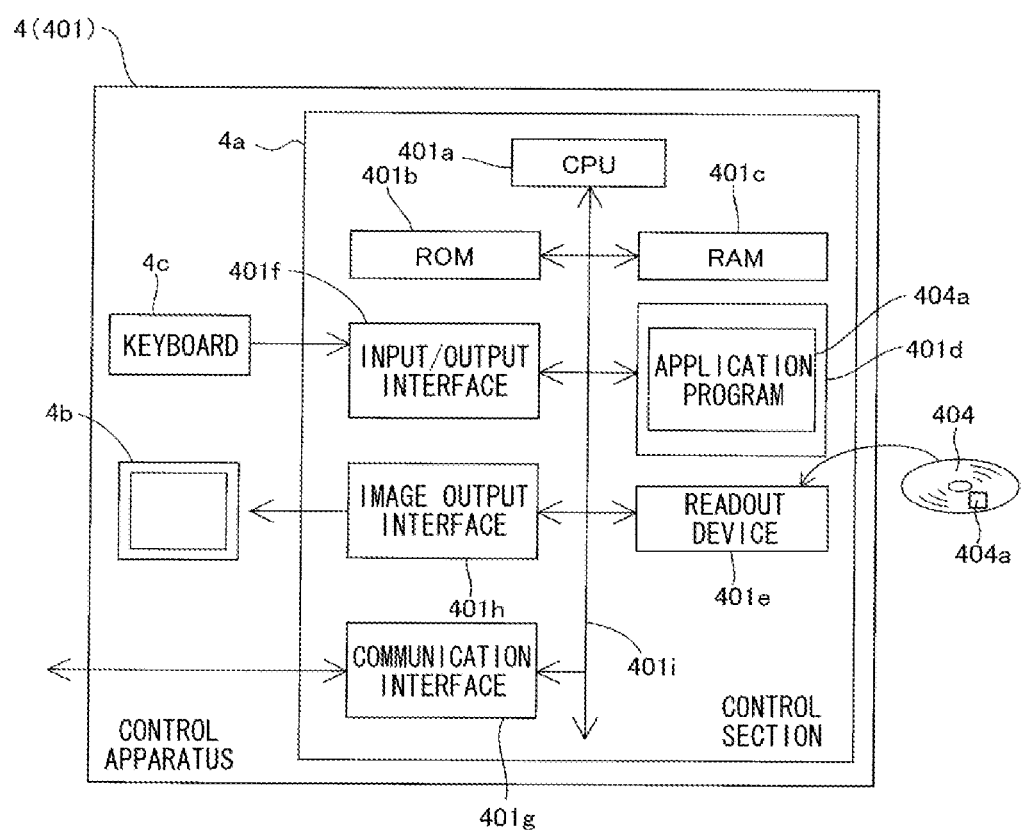
FIG. 5 is a block diagram showing a control apparatus of the analyzer according to the embodiment shown in FIG. 1.

As shown in FIG. 5, the control apparatus 4 is structured as a computer 401 which mainly includes a control section 4a, a display 4b, and a keyboard 4c.

The control section 4a mainly includes a CPU 401a, a ROM 401b, a RAM 401c, a hard disk 401d, a readout device 401e, an input/output interface 401f, a communication interface 401g, and an image output interface 401h. The CPU 401a, ROM 401b, RAM 401c, hard disk 401d, readout device 401e, input/output interface 401f, communication interface 401g, and the image output interface 401h are connected one another via a bus 401i.

The CPU 401a is configured to execute a computer program stored in the ROM 401b and a computer program loaded to the RAM 401c. While the CPU 401a is executing an application program 404a stored in the hard disk 401d, the computer 401 acts as the control apparatus 4.

The ROM 401b is structured as a mask ROM, PROM, EPROM, EEPROM, or the like. The ROM 401b stores computer programs to be executed by the CPU 401a and data to be used for the execution of the computer programs.

The RAM 401c is structured as an SRAM, DRAM, or the like. The RAM 401c is used for loading computer programs stored in the ROM 401b and the hard disk 401d. The RAM 401c is also used as a work area of the CPU 401a at the time of execution of these computer programs.

Various computer programs to be executed by the CPU 401a such as an operating system and the application program 404a, and data to be used for the execution of these computer programs, are installed in the hard disc 401d.

The readout device 401e is structured as a flexible disc drive, CD-ROM drive, DVD-ROM drive, or the like. The readout device 401e is configured to read a computer program or data from a portable storage medium 404. The portable storage medium 404 stores the application program 404a which is used for immunoassay. Thus, the computer 401 can read the application program 404a from the portable storage medium 404 and install the application program 404a in the hard disk 401d.

Note that the application program 404a can be provided to the computer 401 not only via the portable storage medium 404, but also from an external device via a telecommunication line (regardless of whether wired or wireless), which external device is communicably connected to the computer 401 by the telecommunication line. For example, in the case where the application program 404a is stored in a hard disk of a server computer on the Internet, the computer 401 accesses the server computer and downloads the application program 404a from the server computer to install the application program 404a in the hard disk 401d.

Also, an operating system that provides a graphical user interface environment, for example, Windows (registered trademark) manufactured and sold by Microsoft Corporation, is installed in the hard disk 401d.

The input/output interface 401f is configured for example as: a serial interface such as USB, IEEE1394, or RS-232C; a parallel interface such as SCSI, IDE, or IEEE1284; or an analogue interface including a D/A converter, A/D converter, and the like. The keyboard 4c is connected to the input/output interface 401f. A user can input data to the computer 401 by using the keyboard 4c.

The communication interface 401g is an Ethernet (registered-trademark) interface, for example. The computer 401 is configured to transmit/receive data to/from the measurement mechanism unit 2 via the communication interface 401g by using a predetermined communication protocol.

The image output interface 401h is connected to the display 4b which includes an LCD, CRT or the like. The image output interface 401h outputs video signals to the display 4b in accordance with image data supplied from the CPU 401a.

The display 4b is provided for the purpose of displaying analysis results that are obtained based on detection values obtained by the detector 14.

The cuvette feeder 10 is configured to accommodate multiple cuvettes, and has a function to sequentially feed cuvettes one by one to a sample discharging position 1b at which the sample dispensing arm 5 performs a sample discharging operation.

The R1 reagent dispensing arm 6 is configured to aspirate the R1 reagent set at the reagent setting part 16, and to dispense (i.e., discharge) the aspirated R1 reagent into a cuvette placed at the sample discharging position 1b. Referring to FIG. 2, a pipette 6a for aspirating and discharging the R1 reagent is attached to the R1 reagent dispensing arm 6. The R1 reagent dispensing arm 6 has a function to move, to the reaction part 9, a cuvette that has been placed on the sample discharging position 1b by a catcher which is not shown.

The pipette tip feeder 13 has a function to transport pipette tips (not shown) that have been fed into the pipette tip feeder 13 to a tip attaching position one by one, at which position a pipette tip is attached to the sample dispensing arm 5. At the tip attaching position, a pipette tip is attached to the end of the pipette of the sample dispensing arm 5.

The sample dispensing arm 5 has a function to aspirate, after the pipette tip is attached to the pipette at the tip attaching position, a sample from a test tube that has been transported to the sample aspirating position 1a by the sample transporting unit 3, and to dispense (i.e., discharge) at the sample discharging position 1b the sample into a cuvette into which the R1 reagent dispensing arm 6 has dispensed the R1 reagent.

The R2 reagent dispensing arm 7 has a function to aspirate the R2 reagent set at the reagent setting part 16. The R2 reagent dispensing arm 7 is configured to dispense (i.e., discharge) the aspirated R2 reagent into the cuvette that contains the R1 reagent and the sample. Referring to FIG. 2, a pipette 7a for aspirating and discharging the R2 reagent is attached to the R2 reagent dispensing arm 7.

As shown in FIGS. 1, 2, 6 and 7, the reaction part 9 is formed in a round shape and has a hollow center so as to surround the reagent setting part 16 which has a round shape when seen in plan view. Further, the reaction part 9 includes multiple cuvette setting parts 9a which are arranged along the outline of the reaction part 9 with predetermined intervals. The cuvette setting parts 9a are each formed as a round recess which allows a cuvette to be inserted (set) therein. The reaction part 9 has a function to heat the cuvettes set in the cuvette setting parts 9a to approximately 42° C. In other words, in the reaction part 9, samples contained in the cuvettes are heated to approximately 42° C. This prompts reactions to occur between the samples and various reagents in the respective cuvettes. The reaction part 9 is configured to rotate in the clockwise direction (i.e., an arrow A1 direction in FIG. 7), which realizes a function to move the cuvettes set in the cuvette setting parts 9a to respective positions at which various processes (e.g., reagent dispensing) are performed.

The primary BF separator 11 is configured to move, by means of a catcher which is not shown, a cuvette that contains a sample, the R1 reagent, and the R2 reagent from the reaction part 9 to the primary BF separator 11, and to separate the R1 reagent that is unreacted (i.e., an unnecessary component) from magnetic particles in the sample contained in the cuvette (i.e., B/F separation).

The R3 reagent dispensing arm 8 has a function to aspirate the R3 reagent set in the reagent setting part 16. The R3 reagent dispensing arm 8 is configured to dispense (discharge), when a cuvette that contains a sample for which the primary BF separator 11 has performed the B/F separation is moved from the primary BF separator 11 to the reaction part 9, the aspirated R3 reagent into the cuvette. Referring to FIG. 2, a pipette 8a for aspirating and discharging the R3 reagent is attached to the R3 reagent dispensing arm 8.

The secondary BF separator 12 is configured to separate, when the cuvette that contains the R3 reagent and the sample for which the primary BF separator 11 has performed the B/F separation is moved by a catcher (not shown) from the reaction part 9 to the secondary BF separator 12, the R3 reagent that is unreacted (i.e., an unnecessary component) from magnetic particles in the sample contained in the cuvette (i.e., B/F separation).

The R4/R5 reagent feeder 15 is configured to dispense, by means of a tube which is not shown, the R4 reagent and the R5 reagent sequentially into the cuvette that contains the sample for which the secondary BF separator 12 has performed the B/F separation.

The detector 14 obtains, by means of a photo multiplier tube, light that is generated in a reaction process between a luminescent substrate and a labeled antibody bound to an antigen in a sample on which predetermined processes have been performed, thereby measuring the amount of the antigen contained in the sample.

Figure 6:
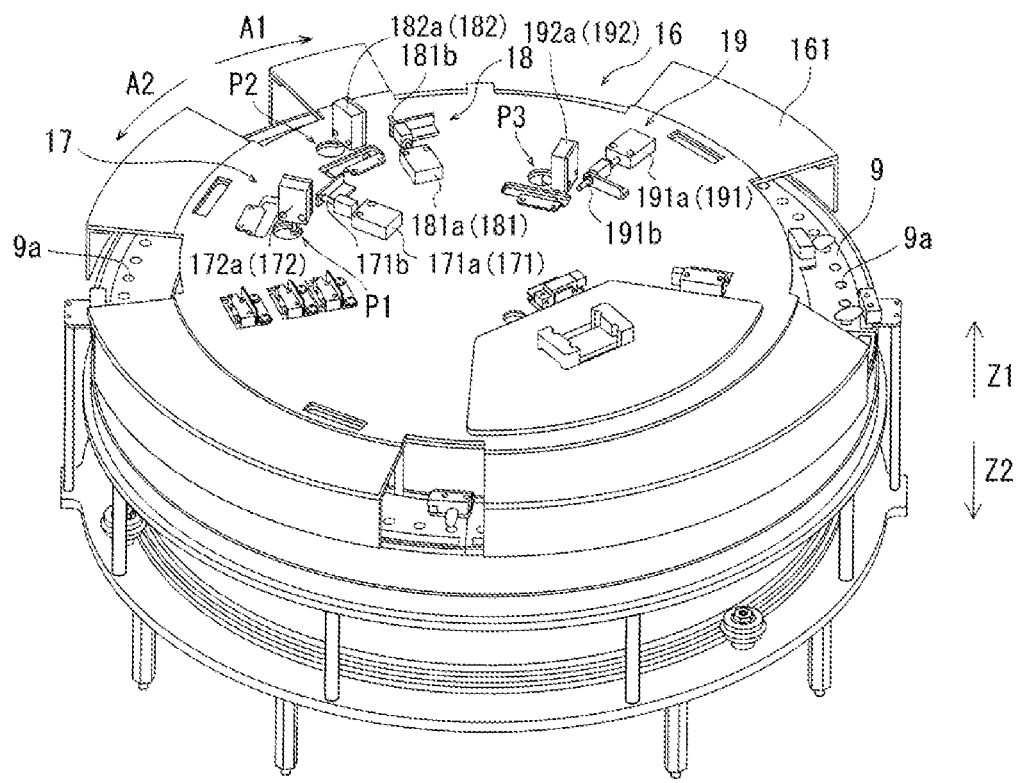
FIG. 6 is a perspective view showing a reagent setting part and a reaction part of the analyzer according to the embodiment shown in FIG. 1.
Figure 7:
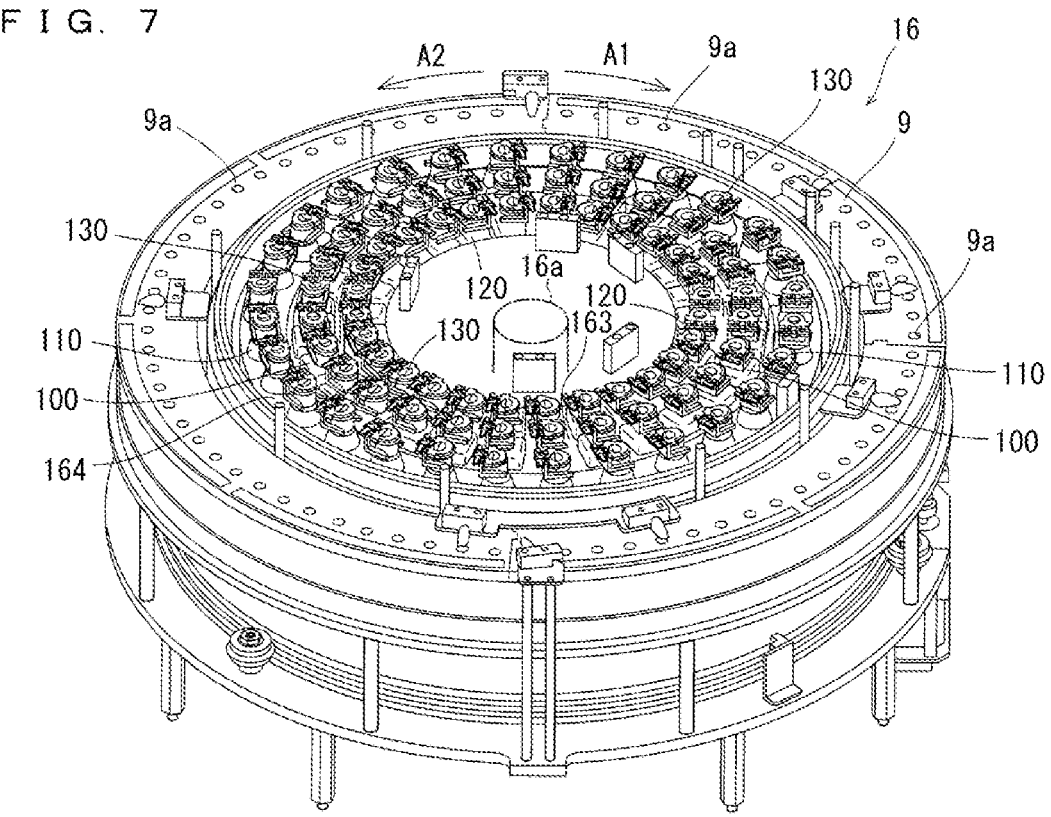
FIG. 7 is a perspective view showing the reagent setting part and the reaction part of the analyzer according to the embodiment shown in FIG. 1.

As shown in FIG. 7, the reagent setting part 16 is provided so as to set therein R1 reagent containers 100 each of which contains the R1 reagent containing a capture antibody, R2 reagent containers 110 each of which contains the R2 reagent containing magnetic particles, and R3 reagent containers 120 each of which contains the R3 reagent containing a labeled antibody. The reagent setting part 16 includes: a cover 161 having a round shape as shown in FIG. 2 and FIG. 6; a bar code reader 162 shown in FIG. 3; an inner table 163 and an outer table 164 shown in FIG. 7; an R1 reagent open/close mechanism 17 shown in FIG. 6; an R2 reagent open/close mechanism 18; and an R3 reagent open/close mechanism 19.

The cover 161 is provided so as to cover both the reagent setting part 16 and the reaction part 9, as shown in FIG. 2 and FIG. 6. The cover 161 having a round shape has openings at predetermined positions through which cuvettes are moved and dispensing operations by the pipettes are performed. The bar code reader 162 has a function to read a bar code (not shown) affixed to each of the reagent containers 100, 110, and 120 set in the reagent setting part 16. Each bar code contains information unique to the corresponding reagent. Note that the bar code reading operation by the bar code reader 162 is performed after the operation check of each mechanism of the measurement mechanism unit 2 and below-described origin position calculations for the tables 163 and 164 are performed at the initialization of the analyzer 1. Information read by the bar code reader 162 is stored in the hard disk 401d of the control apparatus 4 in association with positional information about the reagent containers on the tables 163 and 164.

Figure 8:
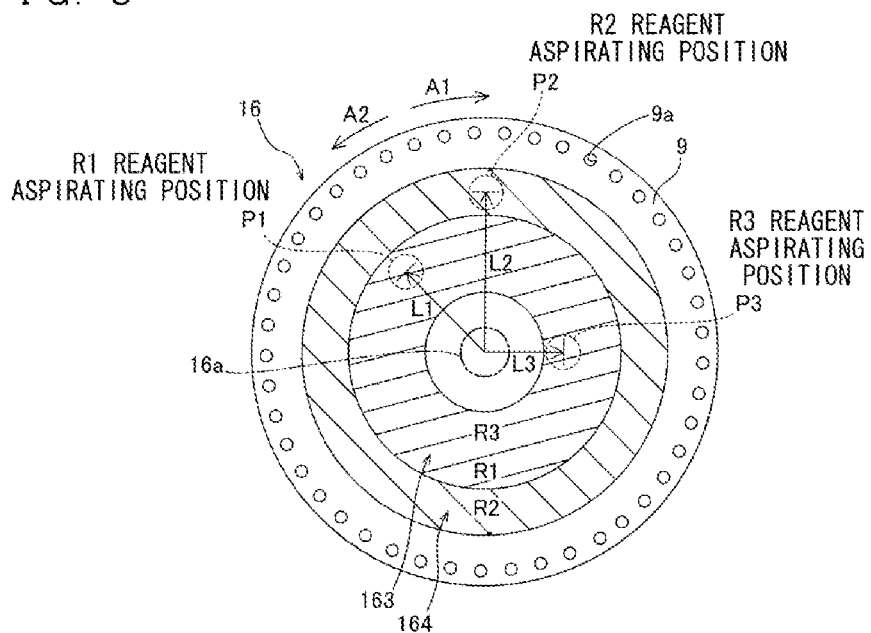
FIG. 8 is a plan view schematically showing the arrangement of the reagent setting part and the reaction part shown in FIG. 7.

As shown in FIG. 7, the inner table 163 is configured to hold multiple R1 reagent containers 100 and multiple R3 reagent containers 120. The inner table 163 is formed in an annular shape and has a hollow center when seen in plan view. The R1 reagent containers 100 are arranged on the inner table 163 in an annular manner so as to surround the R3 reagent containers 120 which are also arranged on the inner table 163 in an annular manner. The R1 reagent containers 100 are disposed so as to be adjacent to the R3 reagent containers 120 in a radial direction. To be specific, as shown in FIG. 8, on the inner table 163, a distance L1 from a below-described rotational axis 16a (i.e., the center of the inner table 163) to each of the R1 reagent containers 100 held in an annular manner is greater than a distance L3 from the rotational axis 16a (i.e., the center of the inner table 163) to each of the R3 reagent containers 120 held in an annular manner. The inner table 163 is configured to horizontally rotate in the clockwise direction (the arrow A1 direction) and in the counterclockwise direction (the arrow A2 direction) with respect to the rotational axis 16a. Specifically, the inner table 163 is configured to rotate with respect to the rotational axis 16a by means of a first stepping motor 163a (see FIG. 3) which is controlled by the control section 2a via a driver board 2e (see FIG. 3). When the inner table 163 rotates, the R1 reagent containers 100 and the R3 reagent containers 120 rotate in the same direction by the same angle. In this manner, the inner table 163 moves an R1 reagent container 100 containing the R1 reagent and an R3 reagent container 120 containing the R3 reagent to a predetermined R1 reagent aspirating position P1 and a predetermined R3 reagent aspirating position P3, respectively.

A first Hall element 163b (see FIG. 3) which includes a magnetic sensor for detecting a magnet (not shown) attached to the reagent setting part 16 is provided at a predetermined position of the inner table 163. The rotary shaft of the first stepping motor 163a is provided with a first encoder 163c which includes an optical sensor for detecting the rotation angle of the first stepping motor 163a. By using the first Hall element 163b and the first encoder 163c, the origin position calculation for the inner table 163 (i.e., positioning of the origin of the inner table 163) is performed.

As shown in FIG. 7 and FIG. 8, the outer table 164 is configured to hold multiple R2 reagent containers 110, and is formed in an annular shape and has a hollow center so as to surround the inner table 163. The outer table 164 can hold the same number of R2 reagent containers 110 as the number of R1 reagent containers 100 and the number of R3 reagent containers 120 which the inner table 163 can hold. The R2 reagent containers 110 are arranged on the outer table 164 in an annular manner so as to surround the R1 reagent containers 100 which are arranged in an annular manner. The outer table 164 is configured to horizontally rotate in the clockwise direction (the arrow A1 direction) and the counterclockwise direction (the arrow A2 direction) with respect to the rotational axis 16a. To be specific, referring to FIG. 9, the outer table 164 is configured to rotate with respect to the rotational axis 16a by means of a second stepping motor 164a (see FIG. 3) which is controlled by the control section 2a via a driver board 2f. As shown in FIG. 8, the outer table 164 is rotatably provided at such a position that a distance L2 from the rotational axis 16a to the outer table 164 (i.e., a distance from the rotational axis 16a to each R2 reagent container 110) is greater than a distance from the rotational axis 16a to the inner table 163. In the present embodiment, the distance L2 from the rotational axis 16a to each R2 reagent container 110 is approximately 175.5 mm. The outer table 164 is rotatable independently of the inner table 163. This allows the outer table 164 to rotate the R2 reagent containers 110 in either direction at any speed without being affected by the speed and direction of the rotation of the R1 reagent containers 100 and the R3 reagent containers 120.

The R2 reagent which contains magnetic particles needs to be agitated in order to uniformly disperse the magnetic particles within the R2 reagent. For this reason, in the present embodiment, the outer table 164 has a function to rotate, thereby agitating the R2 reagent contained in each R2 reagent container 110 held by the outer table 164. The outer table 164 is configured to rotate intermittently, when performing the agitating operation (i.e., when an operation of aspirating the R2 reagent is not performed), in one direction (the arrow A1 direction) with respect to the rotational axis 16a so as to agitate the R2 reagent contained in each R2 reagent container 110. To be specific, referring to FIG. 9, the outer table 164 is configured such that the rotation of the outer table 164 (i.e., the rotational drive of the second stepping motor 164a) is controlled by the driver board 2f applying, based on a control signal outputted from the CPU 2b, a predetermined pulse current (i.e., a pulse signal) to the second stepping motor 164a. The driver board 2f includes a drive pattern storing section 2h which stores types of drive systems (rectangular drive and trapezoidal drive) and setting values such as the number of drive pulses. The CPU 2b sets such setting values.

Thus, the outer table 164 is configured such that two types operations, i.e., an operation of agitating the R2 reagent contained in each R2 reagent container 110 held by the outer table 164 and an operation of moving an R2 reagent container 110 to a predetermined R2 reagent aspirating position P2 at which the R2 reagent dispensing arm 7 aspirates the R2 reagent from the R2 reagent container 110, are controlled by the CPU 2b and the driver board 2f.

In the operation of agitating the R2 reagent, the outer table 164 is rotated intermittently in one direction (the arrow A1 direction), that is, the state of the outer table 164 is periodically switched between being stopped and being rotated in the one direction (the arrow A1 direction). To be more specific, in the R2 reagent agitating operation, the outer table 164 is rotated in the one direction, while an acceleration operation of causing the outer table 164, which is stationary, to start rotating and a deceleration operation of causing the outer table 164 to decelerate to stop rotating are performed alternately. Here, the CPU 2b (i.e., the driver board 2f) is configured to control the driving of the second stepping motor 164a so as to apply to the R2 reagent of each R2 reagent container 110 an inertial force that allows the R2 reagent to be agitated in each R2 reagent container 110. In the present embodiment, the CPU 2b (i.e., the driver board 2f) is configured to drive the second stepping motor 164a so as to switch the state of the outer table 164 between being stopped and being rotated in the one direction (the arrow A1 direction).

Figure 10:
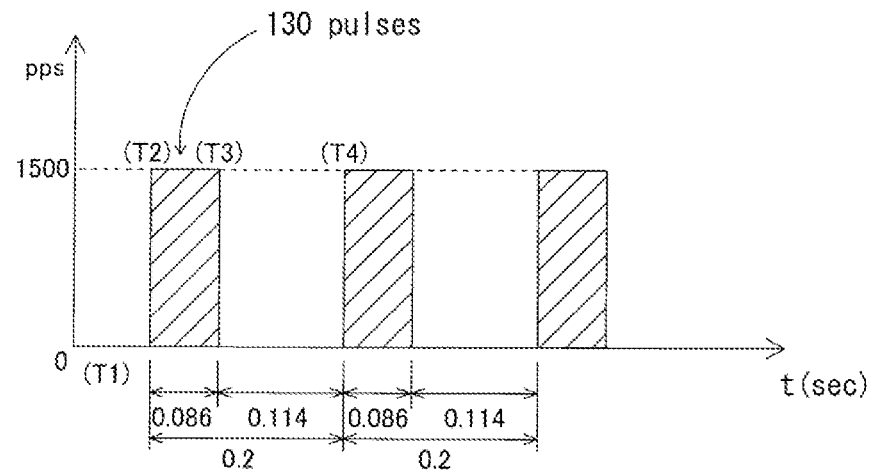
FIG. 10 illustrates control for an agitating operation performed by the outer table of the reagent setting part shown in FIG. 7.

At the R2 reagent agitating operation, the CPU 2b (i.e., the driver board 2f) drives the second stepping motor 164a by the rectangular drive which causes the rotation of the outer table 164 to more rapidly accelerate or decelerate than the trapezoidal drive which is used to drive the second stepping motor 164a to cause the outer table 164 to rotate for the R2 reagent aspirating operation. Specifically, as shown in FIG. 10, the driver board 2f is configured to drive the second stepping motor 164a for a single agitating operation in the following manner: the driver board 2f applies a pulse current to the second stepping motor 164a (i.e., causes the rotation of the outer table 164) at the rate of 1500 pps (pulses per second: the number of pulses applied to a stepping motor per second; hereinafter, "a pulse rate (pps)") for 130 pulses (130/1500=for approximately 0.086 second), and then ceases to apply the pulse current for approximately 0.114 second (i.e., stops the rotation). Here, a change in the driving speed of the second stepping motor 164a during a single agitating operation control is represented by a rectangular shape in FIG. 10. In the single agitating operation control, a pulse current of the pulse rate of 1500 pps is applied to the second stepping motor 164a when the outer table 164 is stationary, and the application of the pulse current is continued for 0.086 second, and then the application of the pulse current to the second stepping motor 164a is ceased for 0.014 second. The driver board 2f (the CPU 2b) is configured to control the driving of the second stepping motor 164a in a manner to repeat a single agitating operation with a period of approximately 0.2 second (0.086 second+0.114 second).

The outer table 164 is configured to rotate in the arrow A1 direction by approximately 3.25 degrees in a single agitating operation in which the second stepping motor 164a is driven by 130 pulses. As described above, the driving of the second stepping motor 164a is instantaneously switched from a state where a pulse current is not applied to the second stepping motor 164a to a state where the pulse current of the pulse rate of 1500 pps is applied to the second stepping motor 164a (or from a state where the pulse current of the pulse rate of 1500 pps is applied to the second stepping motor 164a to a state where a pulse current is not applied to the second stepping motor 164a). Accordingly, the rotational movement of the outer table 164 is such that the outer table 164 rotates in the arrow A1 direction by approximately 3.25 degrees for each single agitating operation, repeating rapid acceleration and a sudden halt periodically. The CPU 2b (i.e., the driver board 2f) is configured to always control the R2 reagent agitating operation except when performing the operation of moving an R2 reagent container 110 to the R2 reagent aspirating position P2 in order for the R2 reagent to be aspirated from the R2 reagent container 110. Accordingly, the outer table 164 is configured to perform, when the analyzer 1 is standing by to perform analysis operations, the R2 reagent agitating operation to uniformly disperse the magnetic particles in each R2 reagent container 110.

In the operation of moving an R2 reagent container 110 to the R2 reagent aspirating position P2, the outer table 164 is caused to rotate in the arrow A1 direction so as to move an R2 reagent container 110 containing the R2 reagent that is to be aspirated to a predetermined position. Here, the CPU 2b (i.e., the driver board 2f) is configured to drive the second stepping motor 164a by trapezoidal drive. To be specific, the CPU 2b (i.e., the driver board 2f) is configured to drive the second stepping motor 164a such that a period in which the outer table 164 rotates includes: an acceleration period in which the outer table 164 rotates with constant acceleration which is less than the acceleration applied to the outer table 164 at the R2 reagent agitating operation (i.e., a period in which the pulse rate (pps) is increased gradually); a constant rotation speed period in which the outer table 164 rotates with a constant speed (i.e., a period in which the pulse rate (pps) is constant); and a deceleration period in which the outer table 164 rotates with constant deceleration which is less than the deceleration applied to the outer table 164 at the R2 reagent agitating operation (i.e., a period in which the pulse rate (pps) is decreased gradually). Note that the length of each of the acceleration period, the constant rotation speed period, and the deceleration period varies depending on the position of an R2 reagent container 110 from which the R2 reagent is to be aspirated (i.e., depending on a distance from the R2 reagent container 110 to the R2 reagent aspirating position P2).

A second Hall element 164b (see FIG. 3) which includes a magnetic sensor for detecting a magnet (not shown) attached to the reagent setting part 16 is provided at a predetermined position of the outer table 164. The rotary shaft of the second stepping motor 164a is provided with a second encoder 164c which includes an optical sensor for detecting the rotation angle of the second stepping motor 164a. By using the second Hall element 164b and the second encoder 164c, the origin position calculation for the outer table 164 (i.e., positioning of the origin of the outer table 164) is performed.

Each of the R1 reagent open/close mechanism 17, the R2 reagent open/close mechanism 18, and the R3 reagent open/close mechanism 19 has the same configuration. Hereinafter, the configuration of the R2 reagent open/close mechanism 18 is described.

Figure 11:
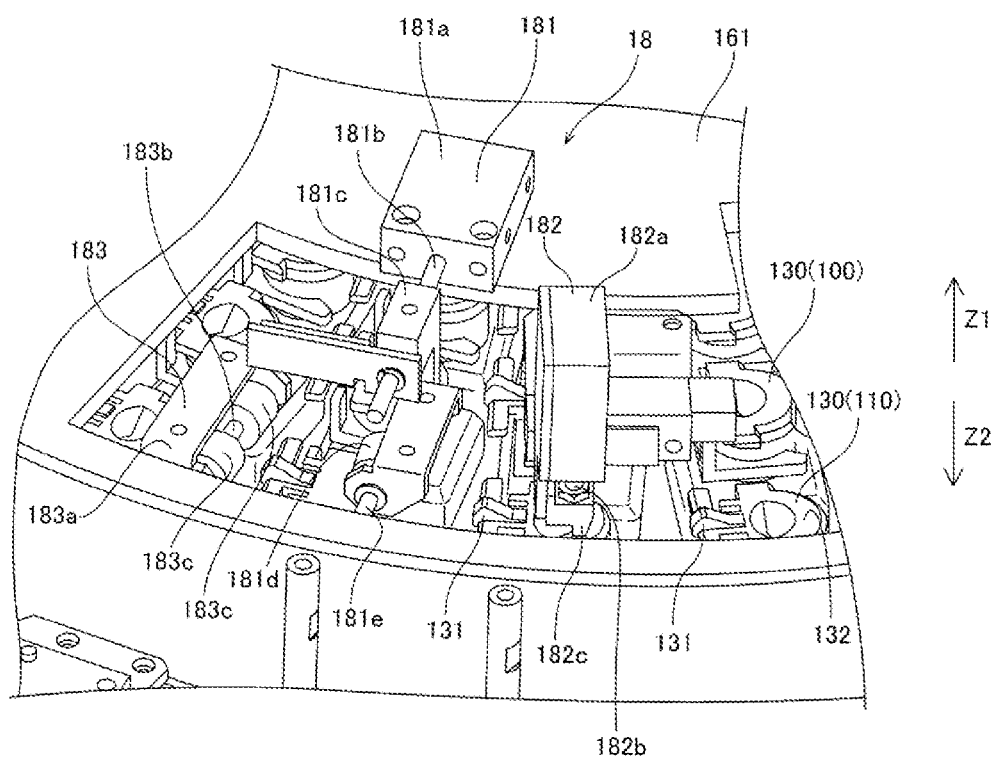
FIG. 11 illustrates a structure of a reagent open/close mechanism of the analyzer according to the embodiment shown in FIG. 1.

As shown in FIG. 11, the R2 reagent open/close mechanism 18 includes an unsealing part 181, a cover moving part 182, and an opening sealing part 183.

The unsealing part 181 includes a third air cylinder 181a set on the cover 161, a shaft 181b, a fitting 181c, an unsealing roller 181d, and a roller shaft 181e. The shaft 181b is disposed so as to extend from the third air cylinder 181a in a radial direction of the cover 161 having a round shape. The roller shaft 181e is disposed so as to extend below the shaft 181b (i.e., at an arrow Z2 direction side) in the radial direction of the cover 161 in parallel to the shaft 181b (i.e., horizontally). The shaft 181b and the roller shaft 181e are connected by the fitting 181c. The unsealing roller 181d is configured to rotate with respect to the roller shaft 181e, which is the rotational center. The unsealing roller 181d is disposed at such a height as to allow the unsealing roller 181d to come in contact with a protruding portion 131 (see FIG. 18) of a below-described cover 130 of an R2 reagent container 110 held by the outer table 164. The unsealing part 181 is configured such that when the third air cylinder 181a is driven, the unsealing roller 181d moves horizontally and linearly in the radial directions of the cover 161 (i.e., an arrow X1 direction and an arrow X2 direction shown in FIG. 15) via the shaft 181b, the fitting 181c, and the roller shaft 181e. This allows the unsealing roller 181d to move to a position where the unsealing roller 181d comes in contact with the protruding portion 131 of the cover 130 and to a position where the unsealing roller 181d does not come in contact with the protruding portion 131.

Figure 18:
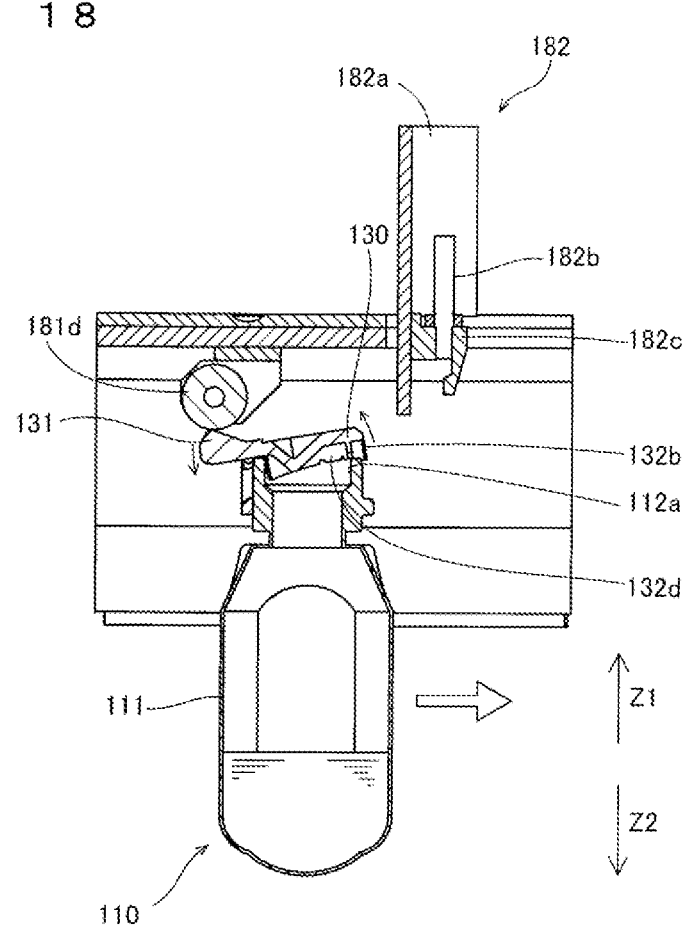
FIG. 18 is a cross-sectional view showing an unsealed state of the R2 reagent container in the reagent aspirating process performed by the analyzer according to the embodiment shown in FIG. 1.

As shown in FIG. 11, the cover moving part 182 includes a fourth air cylinder 182a disposed on the cover 161, a shaft 182b, and a pressing member 182c. Further, as shown in FIG. 18, the shaft 182b is disposed so as to extend from the fourth air cylinder 182a in the downward vertical direction (the arrow Z2 direction), and the pressing member 182c is fitted to the bottom end of the shaft 182b. The pressing member 182c is disposed at a higher elevation than the cover 130 of each R2 reagent container 110 held by the outer table 164 (i.e., disposed at an arrow Z1 direction side with respect to the cover 130). Moreover, the pressing member 182c is, when seen in plan view, disposed on a path along which the protruding portion 131 of each R2 reagent container 110 moves. The cover moving part 182 is configured such that when the fourth air cylinder 182a is driven, the pressing member 182c linearly moves in the vertical directions (i.e., the arrow X1 direction and the arrow X2 direction) via the shaft 182b. Accordingly, the protruding portion 131 of the cover 130 can be pressed downward (in the arrow Z2 direction) by the pressing member 182c when the projecting portion 131 is located at a predetermined position.

Figure 15:
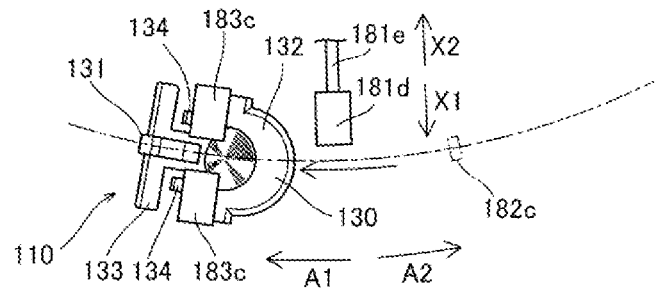
FIG. 15 illustrates operations performed in the reagent aspirating process by the analyzer according to the embodiment shown in FIG. 1.
Figure 16:
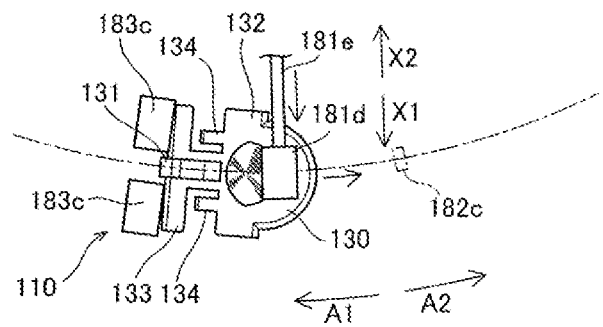
FIG. 16 illustrates operations performed in the reagent aspirating process by the analyzer according to the embodiment shown in FIG. 1.

As shown in FIG. 11, the opening sealing part 183 includes a fitting 183a, a roller shaft 183b, and two rollers 183c. The fitting 183a is attached to the back face of the cover 161 (see FIG. 6). The roller shaft 183b is supported by the fitting 183a. The two rollers 183c are configured to be rotatable with respect to the roller shaft 183b, which is the rotational center. The two rollers 183c are disposed so as to allow the two rollers 183c to come in contact with a below-described top surface 132a (see FIG. 12) of the cover 130 of an R2 reagent container 110 held by the outer table 164. The two rollers 183c have a function to return the state of an R2 reagent container 110 that is being moved in accordance with the rotation of the outer table 164, to a sealed state by coming in contact with the cover 130 of the R2 reagent container 110. In the present embodiment, the opening sealing part 183 is configured to secure the state of each R2 reagent container 110 being sealed by its cover 130, by utilizing the rotation of the outer table 164 with respect to the rotational axis 16a in the arrow A1 direction (i.e., by utilizing the agitating operation and the operation of moving an R2 reagent container 110 to the R2 reagent aspirating position P2). As shown in FIG. 15, the two rollers 183c have a predetermined interval therebetween so as not to come in contact with the protruding portion 131 of the cover 130 of each R2 reagent container 110. Accordingly, when seen in plan view, the protruding portion 131 of each R2 reagent container 110 passes through the space between the two rollers 183c in accordance with the rotation of the outer table 164.

As shown in FIG. 6, an unsealing part 171 of the R1 reagent open/close mechanism 17 and an unsealing part 191 of the R3 reagent open/close mechanism 19 are both equivalent to the unsealing part 181 of the R2 reagent open/close mechanism 18. A first air cylinder 171a of the R1 reagent open/close mechanism 17 and a fifth air cylinder 191a of the R3 reagent open/close mechanism 19 are both equivalent to the third air cylinder 181a of the R2 reagent open/close mechanism 18. A shaft 171b of the R1 reagent open/close mechanism 17 and a shaft 191b of the R3 reagent open/close mechanism 19 are both equivalent to the shaft 181b of the R2 reagent open/close mechanism 18. A cover moving part 172 of the R1 reagent open/close mechanism 17 and a cover moving part 192 of the R3 reagent open/close mechanism 19 are both equivalent to the cover moving part 182 of the R2 reagent open/close mechanism 18. A second air cylinder 172a of the R1 reagent open/close mechanism 17 and a sixth air cylinder 192a of the R3 reagent open/close mechanism 19 are both equivalent to the fourth air cylinder 182a of the R2 reagent open/close mechanism 18. Although not shown, the R1 reagent open/close mechanism 17 and the R3 reagent open/close mechanism 19 both have components equivalent to the following components of the R2 reagent open/close mechanism 18: the fitting 181c, the unsealing roller 181d, and the roller shaft 181e of the unsealing part 181; the shaft 182b and the pressing member 182c of the cover moving part 182; and the fitting 183a, the roller shaft 183b, and the two rollers 183c of the opening sealing part 183.

Hereinafter, a configuration of the R2 reagent container 110 used in the analyzer 1 according to the embodiment of the present invention will be described with reference to FIG. 12 and FIG. 15.

Figure 12:
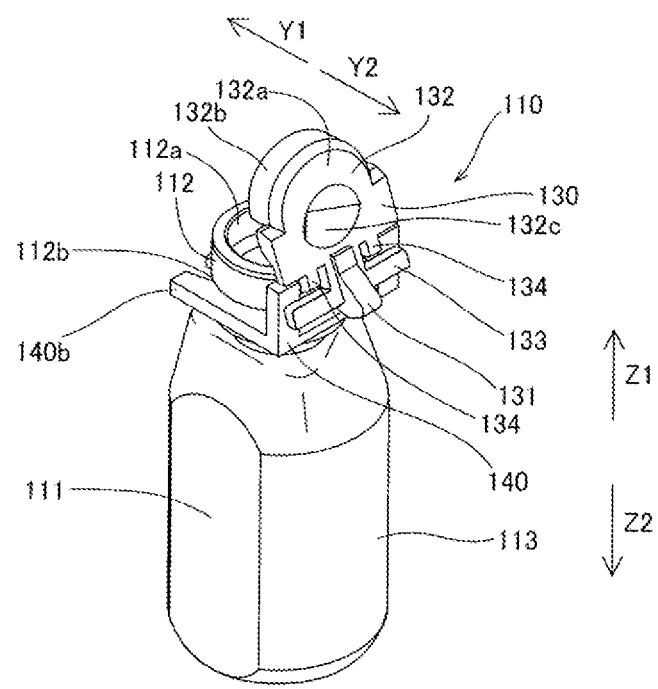
FIG. 12 is a perspective view illustrating a structure of an R2 reagent container used by the analyzer according to the embodiment shown in FIG. 1.

As shown in FIG. 12, the R2 reagent container 110 includes a container body 111, the cover 130 for sealing the container body 111, and a support member 140 for supporting the cover 130 in a manner that allows the cover 130 to pivot.

The container body 111 of the R2 reagent container 110 includes, at its upper side, a cylindrical part 112 which is formed in a substantially cylindrical shape, and includes, at its lower side, a container part 113 for containing a reagent. A round opening 112a is provided at the top end of the cylindrical part 112, and a pair of notch grooves 112b extending horizontally are formed on the side of the cylindrical part 112 in a symmetrical manner. The support member 140 is attached to the container body 111 through the engagement of below-described arms 140b of the support member 140 with the notch grooves 112b.

As shown in FIG. 12, the cover 130 includes the protruding portion 131, a body 132, a base 133 for supporting the protruding portion 131, and a pair of pivoting portions 134. The protruding portion 131 is formed on the base 133 which is substantially T-shaped when seen in plan view. The protruding portion 131 is disposed at the rear side (i.e., at the arrow Y2 direction side) of the cover 130. The protruding portion 131 is formed so as to protrude upward beyond the top surface 132a of the body 132. When seen in plan view, the protruding portion 131 is formed in a rectangular shape which extends in the arrow Y1 and Y2 directions (see FIG. 15) and whose width in the arrow X1 and X2 directions is smaller than the aforementioned interval between the two rollers 183c of the opening sealing part 183.

As shown in FIG. 15, the body 132 is formed such that when seen in plan view, the front half (i.e., the arrow Y1 direction side in FIG. 12) of the body 132 is in a semi-round shape and the rear half of the body 132 is in a rectangular shape. Further, as shown in FIG. 12, the body 132 includes a sidewall 132b which extends downward substantially along the outline of the body 132, and a recess 132c which is formed in a substantially conic shape in the top surface 132a As shown in FIG. 12, the base 133 is substantially T-shaped when seen in plan view (see FIG. 15), and has a function to support the protruding portion 131. The base 133 is disposed at the rear side (i.e., the arrow Y2 direction side) of the body 132.

As shown in FIG. 12, the pair of pivoting portions 134 are formed at the rear side of the body 132 such that they are disposed between the body 132 and the portions of the substantially T-shaped base 133 that extend from side to side. Shaft supports (not shown) are formed in the pivoting portions 134. A pair of shafts (not shown) of the support member 140 are fitted in the shaft supports of the pivoting portions 134. This allows the cover 130 to pivot around the shafts (i.e., around the pivoting portions 134) which act as the pivot center. In this structure, the protruding portion 131 and the body 132 are opposed to each other with respect to the pivot center (i.e., the pivoting portions 134). Therefore, the body 132 can be moved upward by moving the protruding portion 131 downward.

The support member 140 includes a pair of arms 140b. The support member 140 is configured to engage with the cover 130 via the pair of shafts (not shown) in a manner that allows the cover 130 to pivot around the pivoting portions 134. The pair of arms 140b are configured to engage with the notch grooves 112b of the cylindrical part 112 of the container body 111. Accordingly, as shown in FIG. 12, the cover 130 is attached to the cylindrical part 112 of the container body 111 via the support member 140.

Note that each of the R1 reagent container 100 and the R3 reagent container 120 includes the same cover 130 and support member 140 as those of the above-described R2 reagent container 110. Thus, the R1 reagent container 100 and the R3 reagent container 120 are configured such that their covers 130 can be opened/closed by the R1 reagent open/close mechanism 17 and the R3 reagent open/close mechanism 19, respectively, both of which have the same configuration as that of the R2 reagent open/close mechanism 18 which performs opening/closing of the cover 130 of the R2 reagent container 110.

Described next with reference to FIGS. 8 to 10 and FIG. 13 is the R2 reagent agitating operation which is performed by the outer table 164 of the analyzer 1 according to the present embodiment.

Figure 9:
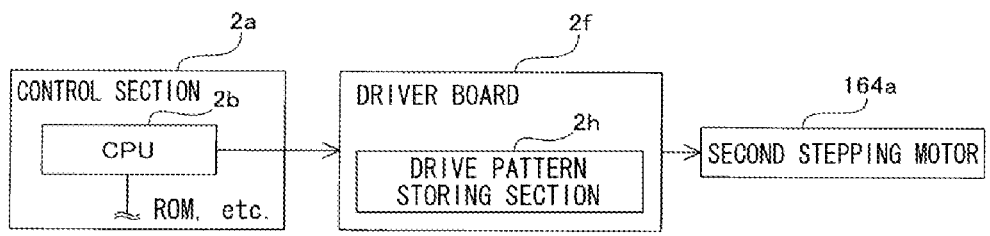
FIG. 9 is a block diagram illustrating a configuration for controlling rotation of an outer table of the reagent setting part shown in FIG. 7.
Figure 13:
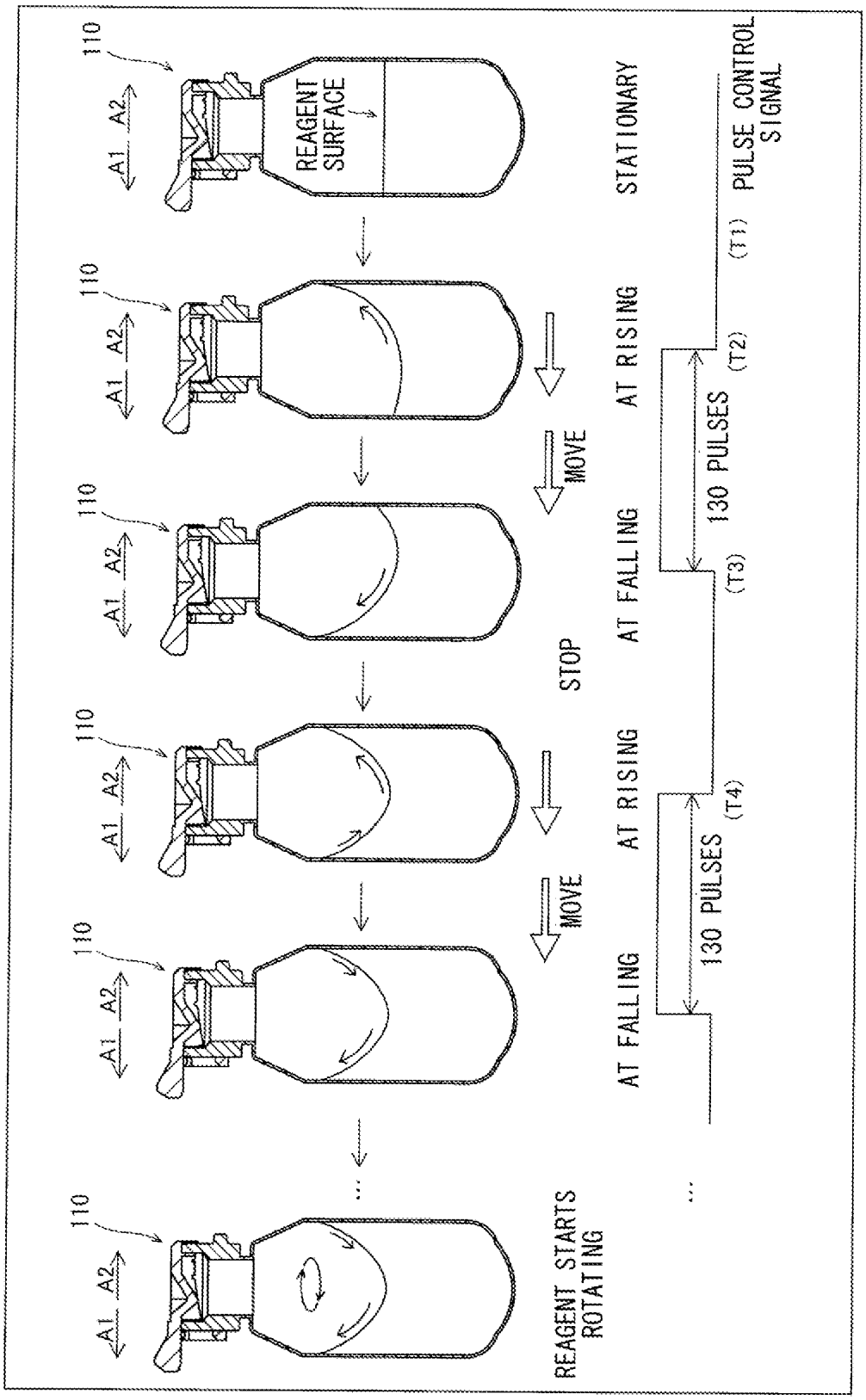
FIG. 13 illustrates the agitating operation performed by the outer table of the analyzer according to the embodiment shown in FIG. 1.
Figure 14:
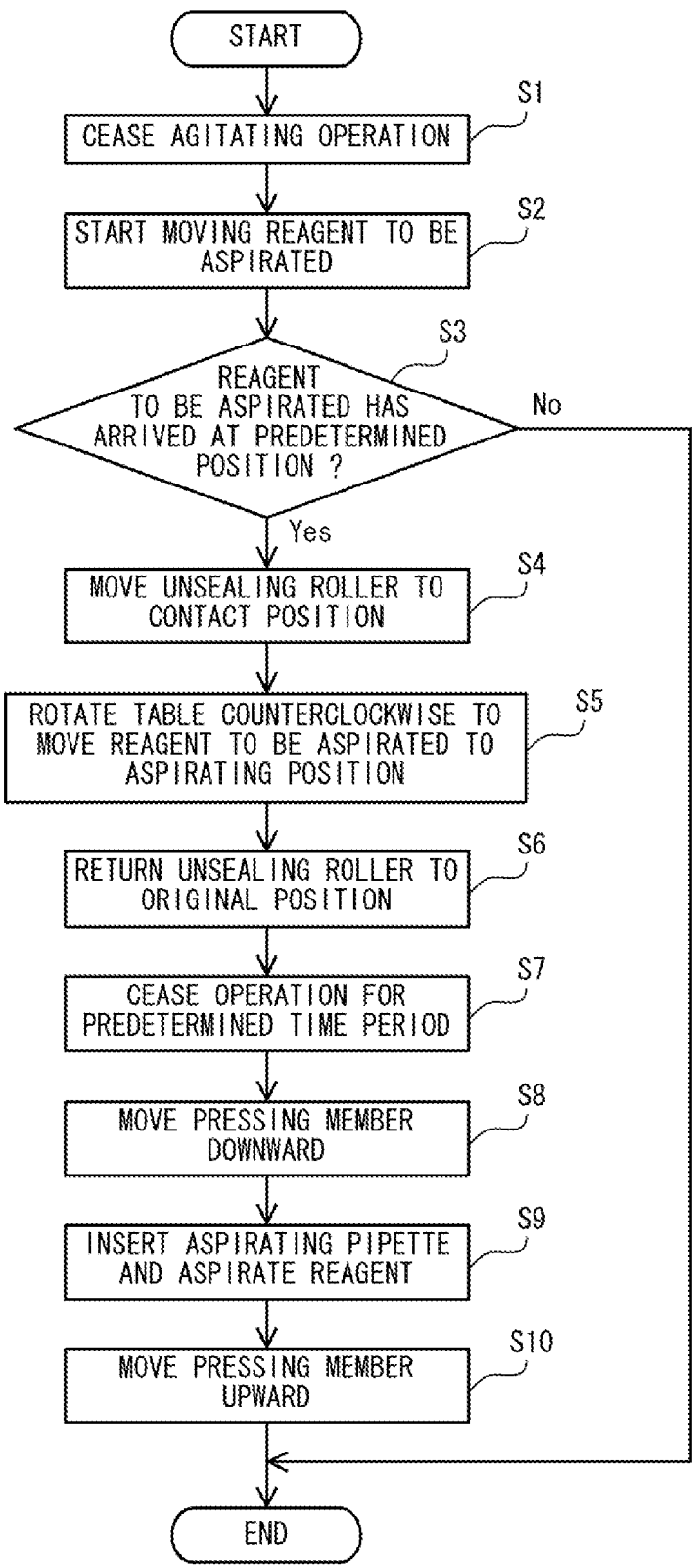
FIG. 14 is a flowchart illustrating operations performed in a reagent aspirating process by the analyzer according to the embodiment shown in FIG. 1.

Referring to FIG. 13, first, at a timing T1, the outer table 164 in its initial state is stationary and the surface of the R2 reagent in the R2 reagent container 110 on the outer table 164 is substantially horizontal. From this state, the R2 reagent agitating operation starts when the driver board 2f applies a pulse current of the pulse rate of 1500 pps to the second stepping motor 164a in accordance with a control signal outputted from the CPU 2b as shown in FIG. 9.

At a timing T2, the rotational speed of the second stepping motor 164a rises to 1500 pps as a result of the driver board 2f having applied the pulse current of the pulse rate of 1500 pps to the second stepping motor 164a. At this timing, as shown in FIG. 10, the state of the second stepping motor 164a is instantaneously switched from the state where a pulse current is not applied thereto to the state where the pulse current of the pulse rate of 1500 pps is applied thereto. Consequently, the outer table 164 starts rotating in the arrow A1 direction with respect to the rotational axis 16a (see FIG. 8) with rapid acceleration. Here, the application of the pulse current of the pulse rate of 1500 pps continues for 0.086 second, during which the rotational speed of the outer table 164 becomes constant. As shown in FIG. 13, although the R2 reagent container 110 moves in the arrow A1 direction in accordance with the rotation of the outer table 164, the R2 reagent in the R2 reagent container 110 tends to remain at rest due to inertia. As a result, the R2 reagent in the R2 reagent container 110 moves (i.e., flows) by being pushed by the inner wall of the R2 reagent container 110 at the side opposite to the moving direction which is the arrow A1 direction (i.e., by the inner wall at the arrow A2 direction side). After the application of the pulse current for approximately 0.086 sec (130 pulses at the rate of 1500 pps) for causing the R2 reagent container 110 to move in the arrow A1 direction has continued, the application of the pulse current to the second stepping motor 164a is ceased at a timing T3. As a result, the outer table 164 rapidly decelerates and stops. Note that the application of the pulse current for approximately 0.086 second (130 pulses at the rate of 1500 pps) from the timing T2 to the timing T3 causes the outer table 164 to rotate with respect to the rotational axis 16a by approximately 3.25 degrees in the arrow A1 direction.

At the timing T3, the rotation of the outer table 164 in the arrow A1 direction comes to a sudden halt due to the ceasing of the application of the pulse current to the second stepping motor 164a. The R2 reagent container 110 stops moving due to the sudden halt of the outer table 164. However, the R2 reagent in the R2 reagent container 110 continues to move in the arrow A1 direction due to inertia. Consequently, the R2 reagent which has been pushed by the inner wall of the R2 reagent container 110 at the side opposite to the moving direction (i.e., by the inner wall at the arrow A2 direction side) moves (flows) relatively in the arrow A1 direction within the R2 reagent container 110, and then dashes against the inner wall of the R2 reagent container 110 at the arrow A1 direction side. Here, the R2 reagent moves in the arrow A1 direction within the R2 reagent container 110, with a part of the R2 reagent left on the inner wall of the R2 reagent container 110 at the arrow A2 direction side due to the viscosity of the R2 reagent, because the R2 reagent has moved in the arrow A2 direction at the timing T2. The ceasing of the application of the pulse current to the second stepping motor 164a continues for approximately 0.114 second, and thus a single agitating operation control is completed. After the ceasing of the application of the pulse current continues for approximately 0.114 second, the driver board 2f (the CPU 2b) starts applying a pulse current of the pulse rate of 1500 pps to the second stepping motor 164a again at a timing T4.

Similar to the timing T2, at the timing T4, the outer table 164 starts rotating in the arrow A1 direction with respect to the rotational axis 16a (see FIG. 8) with rapid acceleration. As a result, the R2 reagent in the R2 reagent container 110 moves (flows) by being pushed, due to inertia, by the inner wall of the R2 reagent container 110 at the side opposite to the moving direction which is the arrow A1 direction (i.e., by the inner wall at the arrow A2 direction side). At this timing, the R2 reagent moves in the arrow A2 direction within the R2 reagent container 110, with a part of the R2 reagent left on the inner wall of the R2 reagent container 110 at the arrow A1 direction side due to the viscosity of the R2 reagent, because the R2 reagent has moved in the arrow A1 direction at the timing T3. In this manner, the R2 reagent in the R2 reagent container 110 is shaken from side to side (between the arrow A1 direction side and the arrow A2 direction side) within the R2 reagent container 110 due to the rapid acceleration and the sudden halt of the outer table 164. As a result, the magnetic particles contained in the R2 reagent start being agitated.

Thereafter, the agitating operation control which includes the application of the pulse current for approximately 0.086 second at the timing T2 (or T4) and the ceasing of the application of the pulse current for approximately 0.114 second at the timing T3 is repeated at a cycle of approximately 0.2 second. As a result, the R2 reagent which is being shaken dashes against the inner wall of the R2 reagent container 110 at both the arrow A1 direction side and the arrow A2 direction side. This causes a recess of an inverted cone shape to be formed at the center of the surface the R2 reagent in the R2 reagent container 110. Further, due to the intermittently repeated rotation of the outer table 164 by approximately 3.25 degrees for each rotation with the radius L2, the R2 reagent flows within the R2 reagent container 110, rotating in a circumferential direction along the inner wall of the R2 reagent container 110. This causes the magnetic particles contained in the reagent of the R2 reagent container 110 to be agitated and dispersed uniformly within the reagent. Further, by performing the agitating operation in this manner, the splatter of the reagent within the reagent container can be suppressed. As described above, the rotation based on 130 pulses causes the outer table 164 to rotate by approximately 3.25 degrees, and the time required to perform a single agitating operation control (i.e., the time for both the application of the pulse current and the ceasing of the application of the pulse current to be performed once) is approximately 0.2 second. Therefore, during the agitating operation, the agitating operation control is performed approximately 111 times (360/3.25) until the outer table 164 fully rotates once. The time required for the agitating operation for one full rotation of the outer table 164 is approximately 22.2 seconds=approximately 0.2× 111.

Next, operations performed in an R2 reagent aspirating process by the analyzer 1 according to the present embodiment are described with reference to FIG. 4 and FIG. 15 to FIG. 21.

In the present embodiment, while the outer table 164 is continuously performing the R2 reagent agitating operation, various processes are performed by respective mechanisms of the measurement mechanism unit 2. That is, in the present embodiment, the R2 reagent agitating operation is always performed except when the operation of moving an R2 reagent container 110 to the R2 reagent aspirating position or the operation of aspirating the R2 reagent by the R2 reagent dispensing arm 7 is being performed. Referring to FIG. 15, during the R2 reagent agitating operation, the R2 reagent container 110 is intermittently rotated in the clockwise direction (the arrow A1 direction). Accordingly, the two rollers 183*c* of the opening sealing part 183 come in contact with the cover 130 of each R2 reagent container 110 and presses the cover 130 from above, thereby preventing the opening 112*a*, which is sealed, from becoming unsealed. At this time, the unsealing roller 181*d* is located so as not to come in contact with the protruding portion 131.

In the R2 reagent aspirating process, first, the R2 reagent agitating operation by the outer table 164 is ceased at step S1. Next, at step S2, the CPU 2*b* of the control section 2*a* (see FIG. 4) causes the outer table 164 to rotate with respect to the rotational axis 16*a* in the arrow A1 direction, so as to start moving an R2 reagent container 110 from which the R2 reagent is to be aspirated. Here, the CPU 2*b* (i.e., the driver board 2*f*) drives the second stepping motor 164*a* of the outer table 164 by trapezoidal drive. The acceleration and deceleration generated by trapezoidal drive for the rotation of the outer table 164 are less than those generated for the rotation of the outer table 164 at the R2 reagent agitating operation.

At step S3, the CPU 2*b* (see FIG. 4) of the control section 2*a* determines whether or not the R2 reagent container 110 from which the R2 reagent is to be aspirated has arrived at a predetermined position. To be specific, referring to FIG. 16, when the protruding portion 131 of the R2 reagent container 110 has passed the unsealing roller 181*d* and arrived at the vicinity of the two rollers 183*c*, the CPU 2*b* determines that the R2 reagent container 110 has arrived at the predetermined position. Next, at step S4, the CPU 2*b* drives the third air cylinder 181*a* to horizontally move the unsealing roller 181*d* to a position at which the unsealing roller 181*d* comes in contact with the protruding portion 131 (see FIG. 16).

Figure 17:
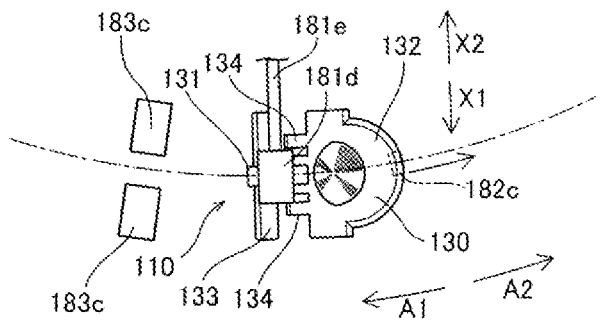
FIG. 17 illustrates operations performed in the reagent aspirating process by the analyzer according to the embodiment shown in FIG. 1.

Then, at step S5, the outer table 164 is rotated in the counterclockwise direction (the arrow A2 direction) so as to move the R2 reagent container 110 to the R2 reagent aspirating position P2. Here, the unsealing roller 181*d* comes in contact with the protruding portion 131 from the body 132 side of the cover 130 as shown in FIG. 17. Thereafter, the R2 reagent container 110 is further moved in the clockwise direction (the arrow A2 direction). As a result, as shown in FIG. 18, the protruding portion 131 side of the cover 130 is gradually pressed downward by the unsealing roller 181*d*. Accordingly, the body 132 side of the cover 130 gradually moves upward. When the unsealing roller 181*d* reaches the top of the protruding portion 131, external air flows into the R2 reagent container 110. As a result, the pressure difference between the inside and outside of the R2 reagent container 110 is eliminated. In this manner, the R2 reagent container 110 becomes unsealed while the cover 130 is still covering the opening 112*a*.

Figure 19:
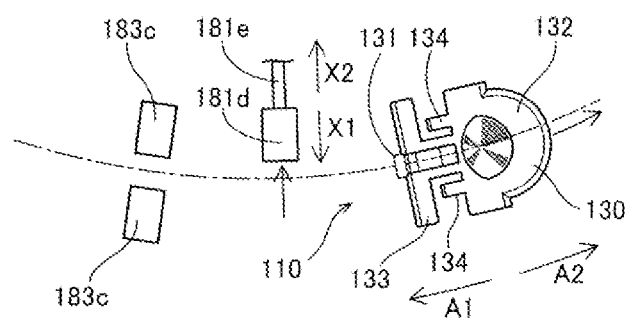
FIG. 19 illustrates operations performed in the reagent aspirating process by the analyzer according to the embodiment shown in FIG. 1.
Figure 20:
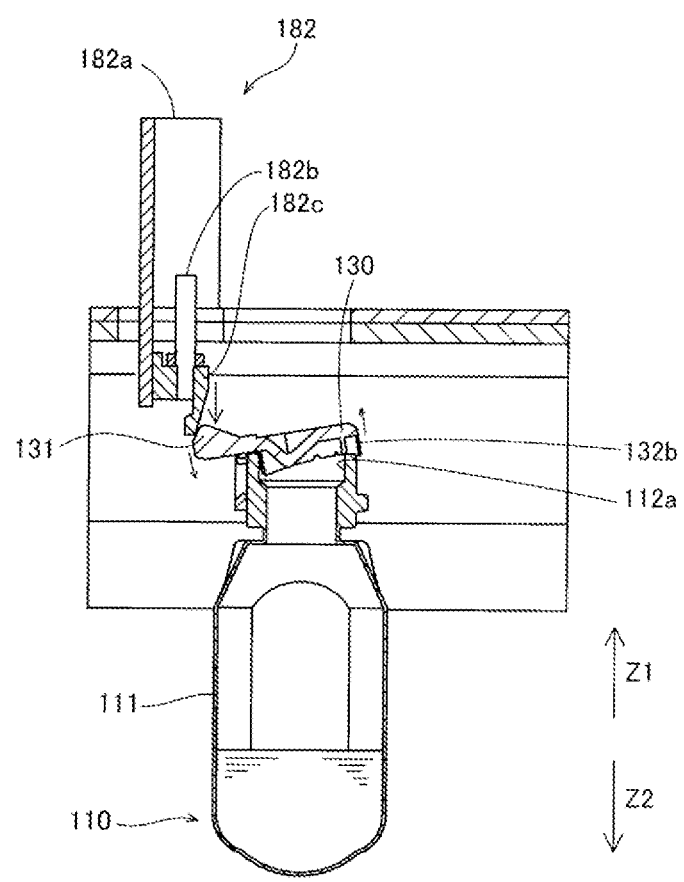
FIG. 20 is a cross-sectional view showing an unsealed state of the R2 reagent container in the reagent aspirating process performed by the analyzer according to the embodiment shown in FIG. 1.
Figure 21:
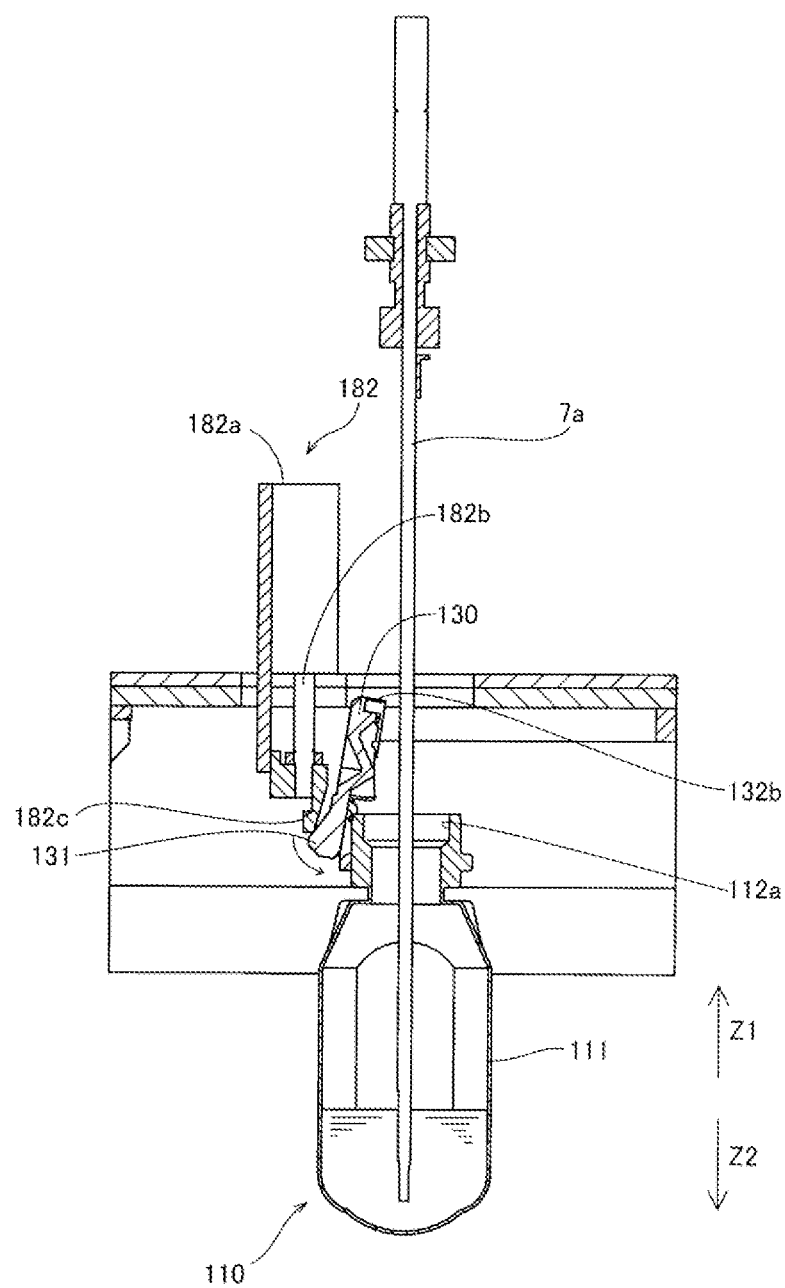
FIG. 21 is a cross-sectional view showing an aspirating operation in the reagent aspirating process performed by the analyzer according to the embodiment shown in FIG. 1.

When the protruding portion 131 of the R2 reagent container 110 has arrived at a position below the pressing member 182*c* (i.e., the R2 reagent aspirating position P2), the unsealing roller 181*d* returns at step S6 to its original position at which the unsealing roller 181*d* does not come in contact with the protruding portion 131 as shown in FIG. 19. Thereafter, the operation is ceased for a predetermined time period at step S7. Then, at step S8, as shown in FIG. 20, the CPU 2*b* drives the fourth air cylinder 182*a* to move the pressing member 182*c* of the cover moving part 182 downward. As a result, the pressing member 182*c* presses the protruding portion 131 downward. When the protruding portion 131 is pressed downward by the pressing member 182*c*, the body 132 side (i.e., the opening 112*a* side) of the cover 130, which is opposed to the protruding portion 131 with respect to the pivot center of the cover 130, moves upward. The cover 130 is moved in this manner until the cover 130 no longer covers the opening 112*a*, whereby the opening 112*a* of the R2 reagent container 110 becomes an opened state as shown in FIG. 21.

Subsequently, at step S9, the pipette 7*a* of the R2 reagent dispensing arm 7 is inserted into the container body 111 of the R2 reagent container 110 through the opening 112*a*, and the pipette 7*a* aspirates a predetermined portion of the R2 reagent. After the predetermined portion of the R2 reagent has been aspirated, the pressing member 182*c* is moved upward at step S10. Accordingly, the opened state of the opening 112*a* is cancelled and the cover 130 is brought back to such a position as to cover the opening 112*a*. This is the end of the operations in the reagent aspirating process.

Thereafter, the CPU 2*b* (i.e., the driver board 2*f*) causes the outer table 164 to rotate in the arrow A1 direction again, so as to start the R2 reagent agitating operation. As a result, the cover 130 of the R2 reagent container 110 which is in an unsealed state comes in contact with the two rollers 183*c* located in the advancing direction of the R2 reagent container 110 (see FIG. 15). Accordingly, the cover 130 is pressed downward and the R2 reagent container 110 returns to the sealed state. The above-described series of operations from step S4 to step S10 are performed within approximately two seconds.

Note that operations performed in a process of aspirating the R1 reagent and operations performed in a process of aspirating the R3 reagent are the same as those performed in the process of aspirating the R2 reagent although ceasing of the agitating operation is not performed for the R1 reagent and the R3 reagent. To be specific, the operations performed in the process of aspirating the R1 reagent or in the process of aspirating the R3 reagent, both of which reagents do not contain magnetic particles, do not include step S1 (i.e., ceasing the agitating operation) but include step S2 and the steps thereafter. Further, in the operations performed in the process of aspirating the R1 reagent or in the process of aspirating the R3 reagent, the inner table 163 rotates independently of the outer table 164, thereby moving an R1 reagent container 100 or an R3 reagent container 120 to the R1 reagent aspirating position P1 or the R3 reagent aspirating position P3, respectively.

In the present embodiment, when the above-described reagent aspirating operation is not performed, the CPU 2b (i.e., the driver board 2f) controls the second stepping motor 164a to cause the outer table 164 to rotate in the arrow A1 direction while alternately performing the acceleration (i.e., a switch from the state where the pulse current application is ceased to the state where the pulse current of the pulse rate of 1500 pps is applied) and the deceleration (i.e., a switch from the state where the pulse current of the pulse rate of 1500 pps is applied to the state where the pulse current application is ceased). The R2 reagent in the R2 reagent container 110 can be agitated by merely causing the outer table 164 to rotate in the arrow A1 direction intermittently with the alternate acceleration and deceleration. To be specific, when the outer table 164 rotates with the alternate acceleration and deceleration, the R2 reagent in the R2 reagent container 110 tends to maintain, due to inertia, its moving speed before the rotation is accelerated and its moving speed before the rotation is decelerated. Accordingly, with changes in the moving speed of the R2 reagent container 110, the R2 reagent in the R2 reagent container 110 can be caused to flow relative to the R2 reagent container 110. As a result of the R2 reagent flowing in this manner, the R2 reagent can be agitated effectively. This allows the structure of the analyzer 1 to be simplified as compared to a case where a structure for causing each reagent container to rotate on its axis is provided at the outer table. Thus, the analyzer 1 according to the embodiment of the present invention realizes a simplified analyzer structure and allows the R2 reagent contained in each R2 reagent container 110 to be agitated effectively.

As described above, in the present embodiment, the CPU 2b (i.e., the driver board 2f) controls the second stepping motor 164a such that the outer table 164 rotates intermittently in the arrow A1 direction based on the switching of the state of the outer table 164 between the state where the rotation is ceased (i.e., a rotation ceased state) and the state where the outer table 164 rotates at the pulse rate of 1500 pps (i.e., a rotating state). This allows a great difference in speed to be readily produced between the rotation ceased state and the rotating state. That is, by using the acceleration from the rotation ceased state to the rotating state at the pulse rate of 1500 pps and the deceleration from the rotating state at the pulse rate of 1500 pps to the rotation ceased state, the acceleration and the deceleration can be readily increased without increasing the speed of the rotation during the rotating state. This makes it possible to readily apply a great inertial force to the R2 reagent in the R2 reagent container 110.

Moreover, in the above-described embodiment, the CPU 2b (i.e., the driver board 2f) controls the second stepping motor 164a such that the state where the pulse current application to the second stepping motor 164a is ceased continues for approximately 0.114 second and the state where the pulse current of the pulse rate of 1500 pps is applied to the second stepping motor 164a continues for approximately 0.086 second. Accordingly, the rotation ceased state and the rotating state of the outer table 164 are switched within a short time period. Therefore, as shown in FIG. 13, the R2 reagent can be agitated while preventing the flow of the R2 reagent moving (flowing) within the R2 reagent container 110 from becoming calm. Thus, the R2 reagent in the R2 reagent container 110 can be agitated more effectively as compared to a case, for example, where a pulse current is applied to the stepping motor to cause the reagent to flow within the reagent container, and after the flow of the reagent has become calm, the application of the pulse current to the stepping motor is ceased.

Further, in the above-described embodiment, during a period in which the R2 reagent is not aspirated, the CPU 2b (i.e., the driver board 2f) drives the second stepping motor 164a by the above-described rectangular drive in order to: start applying the pulse current of the pulse rate of 1500 pps to the second stepping motor 164a to which the pulse current has not been applied, thereby causing the outer table 164 to rotate; and then cease to apply the pulse current to the second stepping motor 164a. In this manner, the speed of the rotation of the outer table 164 can be quickly changed. This allows a great inertial force to be applied to the R2 reagent in the R2 reagent container 110. Consequently, the R2 reagent can be effectively caused to move (flow) within the R2 reagent container 110. Thus, the R2 reagent can be agitated effectively.

Furthermore, in the above-described embodiment, when the R2 reagent is to be aspirated, the CPU 2b (i.e., the driver board 2f) controls the second stepping motor 164a by trapezoidal drive such that a period in which the outer table 164 rotates includes: an acceleration period in which the outer table 164 rotates with constant acceleration which is less than the acceleration applied to the outer table 164 at the R2 reagent agitating operation (i.e., a period in which the pulse rate is increased gradually); and a deceleration period in which the outer table 164 rotates with constant deceleration which is less than the deceleration applied to the outer table 164 at the R2 reagent agitating operation (i.e., a period in which the pulse rate is decreased gradually). In this manner, changes in the moving speed of the outer table 164 can be made gradual as compared to the changes in the moving speed of the outer table 164 that are caused by the acceleration and deceleration at the R2 reagent agitating operation. As a result, when the R2 reagent container 110 is to be moved to the R2 reagent aspirating position P2, the outer table 164 can be precisely controlled to stop rotating so as to locate the R2 reagent container 110 at the R2 reagent aspirating position P2. Accordingly, the R2 reagent container 110 can be precisely located at the R2 reagent aspirating position P2.

Still further, in the above-described embodiment, the CPU 2b (i.e., the driver board 2f) repeatedly and periodically switches the state of the second stepping motor 164a between the state where the pulse current application to the second stepping motor 164a is ceased and the state where the pulse current of the pulse rate of 1500 pps is applied to the second stepping motor 164a. In this manner, the R2 reagent can be effectively caused to move (flow) within the R2 reagent container 110. Owing to the periodic switching of the state of the second stepping motor 164a, the R2 reagent can be caused to continue flowing within the R2 reagent container 110. This allows the agitated state of the R2 reagent to be maintained.

Still further, in the above-described embodiment, the opening sealing part 183 (i.e., the rollers 183c) is provided, which performs the sealing of the opening 112a of the R2 reagent container 110 by utilizing the cover 130 of the R2 reagent container 110 being moved in accordance with the horizontal rotation of the outer table 164 in the arrow A1 direction with respect to the rotational axis 16a. Therefore, the opening 112a of the R2 reagent container 110 can be sealed by merely causing the outer table 164 to rotate in the arrow A1 direction.

Note that the embodiment disclosed herein is merely illustrative in all aspects and should not be recognized as being restrictive. The scope of the present invention is defined not by the description of the above embodiment but by the scope of the claims, and includes meaning equivalent to the scope of the claims and all modifications within the scope.

For example, the above embodiment describes a case where the outer table 164 centering around the rotational axis 16a is disposed outside the inner table 163. However, the present invention is not limited thereto. For instance, the outer table and the inner table may be configured as separate reagent container holders which rotate with respect to different rotational axes, respectively.

The above embodiment describes, as an example of a sample analyzer, an analyzer that includes a reagent setting part that can hold three types of reagent containers, that is, R1 reagent containers, R2 reagent containers, and R3 reagent containers. However, the present invention is not limited thereto. The sample analyzer may be an analyzer that includes a reagent setting part for holding one or two types of reagent containers, or may be an analyzer that includes a reagent setting part for holding four or more types of reagent containers.

Although the above embodiment gives an example in which a stepping motor causes the outer table to rotate with respect to the rotational axis, the present invention is not limited thereto. For example, other than a stepping motor, a servomotor or the like may be used to cause the outer table to rotate.

In the above embodiment, the pulse current of the pulse rate of 1500 pps is applied to the second stepping motor 164a when the operation of agitating the R2 reagent container is performed. However, the present invention is not limited thereto. For example, other than the pulse current of the pulse rate of 1500 pps, a pulse current of the pulse rate of 2000 pps or the pulse rate of 1000 pps may be applied to the second stepping motor 164a.

The above embodiment gives an example in which the state of the second stepping motor 164a is switched between the state where a pulse current is not applied thereto and the state where the pulse current of the pulse rate of 1500 pps is applied thereto. However, the present invention is not limited thereto. For example, the R2 reagent agitating operation may be performed by switching the state of the second stepping motor 164a between the state where a pulse current of the pulse rate of 150 pps is applied to the second stepping motor 164a and the state where a pulse current of the pulse rate of 1500 pps is applied to the second stepping motor 164a. In such a case, a great inertial force can be applied to the R2 reagent in the R2 reagent container 110 while keeping the outer table 164 rotating (i.e., while preventing the outer table 164 from stopping). In this manner, the R2 reagent can be effectively agitated without causing the rotation of the outer table 164 to stop.

Further, the above embodiment describes a configuration in which the second stepping motor 164a is driven by the above-described rectangular drive at the R2 reagent agitating operation so as to cause the outer table 164 to rapidly accelerate and come to a sudden halt. However, the present invention is not limited thereto. In the present invention, it is only necessary for each of the acceleration and the deceleration of the outer table to have a predetermined magnitude or greater. Moreover, in the present invention, the second stepping motor 164a need not be driven by rectangular drive at the agitating operation. If the acceleration and the deceleration of the outer table both have a predetermined magnitude or greater, effective agitation can be realized even if the agitating operation is performed by trapezoidal drive.

Still further, the above embodiment gives an example in which at the agitating operation, the state where the pulse current is applied to the second stepping motor 164a continues for approximately 0.086 second and the state where the pulse current application to the second stepping motor 164a is ceased continues for approximately 0.114 second. Thus, the length of a single agitating operation is approximately 0.2 second. However, the present invention is not limited thereto. In the present invention, the state where the pulse current is applied to the second stepping motor 164a may continue for a time period different from approximately 0.086 second. Also, the state where the pulse current application to the second stepping motor 164a is ceased may continue for a time period different from approximately 0.114 second. Furthermore, a time period different from approximately 0.2 second may be the length of a single agitating operation. These values may be changed as necessary in accordance with the conditions such as the viscosity and amount of the reagent, the size and shape of the reagent container, etc. However, it is preferred that the state where the pulse current is applied to the second stepping motor 164a continues for 0.08 second or longer, and the state where the pulse current application to the second stepping motor 164a is ceased continues for 0.15 second or shorter.

Still further, the above embodiment gives an example in which a single agitating operation including the rotating state and the rotation ceased state of the outer table 164 is repeated periodically. However, the present invention is not limited thereto. In the present invention, the agitating operation by the outer table need not be performed periodically. So long as changes in the speed of the rotation of the outer table (i.e., acceleration and deceleration) allow the R2 reagent to be agitated, the changes in the speed may occur in a non-periodic manner.

Still further, the above embodiment gives an example where in each single agitating operation, the outer table 164 rotates by approximately 3.25 degrees, which is caused by 130 pulses applied to the second stepping motor 164a. However, the present invention is not limited thereto. In the present invention, the outer table may be configured to rotate, in each single agitating operation, by an angle different from 3.25 degrees, which angle may be up to approximately 5 degrees, or alternatively, up to approximately 10 degrees. In such a case, the number of pulses for driving the second stepping motor 164a to rotate need not be 130 pulses. The second stepping motor 164a may be driven by the number of pulses that is different from 130 pulses. An angle by which the outer table rotates based on the rotational driving of the second stepping motor 164a for one pulse may be changed.

In the above embodiment, in the R2 reagent aspirating process, the R2 reagent container is moved to and then located at a predetermined position. At this time, the speed of the rotation of the outer table is not reduced at a position other than the predetermined position. However, the present invention is not limited thereto. For example, similar to the R2 reagent agitating operation, when the R2 reagent aspirating process is performed, the outer table may be intermittently rotated to locate the R2 reagent container at the predetermined position.

The above embodiment gives an example in which the outer table 164 always performs the agitating operation except when the operation of aspirating the R2 reagent is performed. However, the present invention is not limited thereto. For example, the outer table 164 may be configured to perform the agitating operation at regular intervals. Moreover, when the R2 reagent is to be aspirated, the outer table 164 may perform the agitating operation prior to the R2 reagent aspirating process, for example.

Further, the above embodiment gives an example in which the sealing of the R2 reagent container 110 by the cover 130 is performed by the two rollers 183c of the opening sealing part 183 by utilizing the rotation of the outer table 164. However, the present invention is not limited thereto. In the present invention, the cover 130 of the R2 reagent container 110 may be opened by utilizing the rotation of the outer table 164. For example, the cover 130 of the R2 reagent container 110 may be sealed by utilizing the rotation of the outer table 164 in the arrow A1 direction, and the cover 130 of the R2 reagent container 110 may be opened by utilizing the rotation of the outer table 164 in the arrow A2 direction.

In the above embodiment, the opening 112a is unsealed by the unsealing part 181, and the opening 112a is fully opened by the cover moving part 182. However, the present invention is not limited thereto. For example, the operation of unsealing the opening 112a and the operation of fully opening the opening 112a may be performed by a single mechanism.

The above embodiment describes the CPU and the driver board of the measurement mechanism unit as an example of a controller for controlling a driver that causes the outer table to rotate. However, the present invention is not limited thereto. The driver for causing the outer table to rotate may be controlled by the CPU and the driver board of the control apparatus. In such a case, each mechanism of the measurement mechanism unit and the sample transporting unit may be controlled by the CPU of the control apparatus.

The embodiment of the present invention can be variously modified within the scope of the technical idea disclosed in the appended claims.

What is claimed is:

1. A sample analyzing method comprising:
    setting a first reagent container containing a first reagent on a first reagent container holder, which is configured to rotate around a rotational axis while holding the first reagent container, wherein the first reagent contains magnetic particles;
    setting a second reagent container containing a second reagent on a second reagent container holder, which is configured to rotate around the rotational axis independently from the first reagent container holder while holding the second reagent container, wherein the second reagent does not contain magnetic particles;
    in a first rotation operation, rotating the first reagent container holder to alternately repeat a first acceleration in a rotational direction and a first deceleration in the same rotational direction when the first reagent is not needed to be aspirated;
    in a second rotation operation, rotating the first reagent container holder to locate the first reagent container at a first reagent aspirating position by causing the first reagent container holder to accelerate with a second acceleration to start rotating and causing the first reagent container holder to decelerate with a second deceleration to stop rotating; wherein the first acceleration is greater than the second acceleration and the first deceleration is greater than the second deceleration;
    in a third rotation operation, rotating the second reagent container holder to locate the second reagent container at a second reagent aspirating position; and
    analyzing a measurement sample that is prepared from a sample, the first reagent, and the second reagent, the first reagent being aspirated from the first reagent container located at the first reagent aspirating position and the second reagent being aspirated from the second reagent container located at the second reagent aspirating position.

2. The sample analyzing method of claim 1, wherein
    the first rotation operation comprises periodically switching the first acceleration and the first deceleration.

3. The sample analyzing method of claim 1, wherein the second reagent container holder does not rotate during the first rotation operation.

4. The sample analyzing method of claim 1, wherein
    the first rotation operation comprises periodically repeating a start and a stop of a rotation of the first reagent container holder.

5. The sample analyzing method of claim 1, wherein the first reagent container holder is configured to rotate in response to being driven by a first driver according to drive pulses applied to the first driver,
    the second reagent container holder is configured to rotate in response to being driven by a second driver according to drive pulses applied to the second driver, and
    a controller is programmed to periodically apply a predetermined number of drive pulses to the first driver to cause the first reagent container holder to repeat the first acceleration and the first deceleration.

6. The sample analyzing method of claim 5, wherein the second rotation operation comprises gradually increasing and decreasing the rate of drive pulses applied to the first driver, to locate the first reagent container held by the first reagent container holder at the first aspirating position.

7. The sample analyzing method of claim 1, wherein
    a distance from the rotational axis to the first container aspirating position is greater than a distance from the rotational axis to the second container aspirating position.

8. The sample analyzing method of claim 1, wherein
    the first reagent container holder is configured to hold a plurality of reagent containers in an annular arrangement.

* * * * *